United States Patent [19]

Mori et al.

[11] Patent Number: 5,756,315
[45] Date of Patent: May 26, 1998

[54] INOSINE-GUANOSINE KINASE

[75] Inventors: Hideo Mori; Akihiro Iida; Sadao Teshiba, all of Machida; Tatsuro Fujio, Hofu, all of Japan

[73] Assignee: Kyowa Hakko Kogyo Co., Ltd., Tokyo, Japan

[21] Appl. No.: 404,127

[22] Filed: Mar. 14, 1995

Related U.S. Application Data

[63] Continuation of Ser. No. 253,224, Jun. 2, 1994, abandoned, which is a continuation of Ser. No. 730,827, Aug. 2, 1991, abandoned.

[30] Foreign Application Priority Data

Dec. 5, 1989 [JP] Japan ...................................... 1-315537

[51] Int. Cl.$^6$ .............................. C12N 15/55; C12N 9/16; C12N 15/63; C12P 19/32
[52] U.S. Cl. ..................... 435/89; 435/196; 435/252.3; 435/252.33; 435/320.1; 536/23.2
[58] Field of Search .................... 435/69.1, 68.1, 435/69.2, 89, 196, 252.3, 320.1, 252.33; 536/23.2

[56] References Cited

FOREIGN PATENT DOCUMENTS 57-110194  7/1982  Japan .

OTHER PUBLICATIONS

Hove–Jensen, J. Gen. Microbiol., 135 (1989) 1263–73.
Pierre and LePage, Formation of Inosine 5'–Monophosphate by a Kinase . . . Proc. Soc. Exp. Biol. Med. 127: 432–440 (1968).

No new references are cited. Please see PTOL 892 attached to paper 11.

Jochimsen et al (1975) Mol. Gen–Genct 143:85–91. "Location on the chromosome of *E. coli* of genes governing purine metabolism . . . ".

Kohara et al (1987) Cell 50:495–508. "The physical map of the whole *E. coli* chromosome: Application of a new strategy . . . ".

Maniatis et al Mol. Cloning Cold Spring Press (1982).

Combes et al Plant Phys Biochem (Paris) 27(5) 729–36 1989.

LePage et al. Pro Soc. Exp. Md. 127(1) 237–244 (1968).

Maniatis et al. *Molecular Cloning* Cold Springs Harbor Press (1982).

Combes et al Plant Physiol. Biochem (Paris) 27(5) 729–36 (1989).

LePage et al. Pro. soc. Exp. Med 127(1) 239–44 (1968).

*Primary Examiner*—Rebecca E. Prouty
*Attorney, Agent, or Firm*—Fitzpatrick, Cella, Harper & Scinto

[57] ABSTRACT

The present invention relates to an inosine-guanosine kinase which catalyzes the reaction of forming 5'-inosinic acid (5'-IMP) from inosine and adenosine triphosphate (ATP) or deoxyadenosine triphosphate (dATP) and the reaction of forming 5'-guanylic acid (5'-GMP) from guanosine and ATP or dATP.

12 Claims, 8 Drawing Sheets

INOSINE-GUANOSINE KINASE

This application is a continuation of application Ser. No. 08/253,224, filed Jun. 2, 1994, now abandoned, which is a continuation of application Ser No. 07/730,827, filed Aug. 2, 1991, now abandoned.

TECHNICAL FIELD

The present invention relates to an inosine-guanosine kinase which catalyzes the reaction of forming 5'-inosinic acid (5'-IMP) from inosine and adenosine triphosphate (ATP) or deoxyadenosine triphosphate (dATP) and the reaction of forming 5'-guanylic acid (5'-GMP) from guanosine and ATP or dATP, and to a process for producing 5'-nucleotides using the enzyme.

BACKGROUND ART

5'-Nucleotides, inter alia, 5'-IMP and 5'-GMP have a flavor enhancing activity and are widely used as a seasoning agent. As the method for producing 5'-nucleotides, there are known a method for enzymatically decomposing RNA present in yeast cells (Journal of Agricultural and Chemical Society of Japan, 34, 489, 1969), a method for culturing a microorganism having an ability to produce 5'-IMP [Agricultural and Biological Chemistry, 46, 2557 (1982)], a method for chemical phosphorylation of nucleosides such as inosine and guanosine [Bulletin of the Chemical Society of Japan, 42, 3505-3508 (1969)], and the like. Currently, it is considered that the chemical phosphorylation utilizing these nucleosides would be the most advantageous from an industrial standpoint, because inosine and guanosine are easily obtained by fermentation However, in the case of performing chemical phosphorylation, large quantities of chlorides are used at a lower temperature [Bulletin of the Chemical Society of Japan, 42, 3505-3508 (1969)] so that the method is not desired from viewpoints of both costs and environmental hygiene. Accordingly, enzymatic phosphorylation of nucleosides under mild conditions is desired. Hitherto, biochemical phosphorylation of purine nucleosides using cultured cells of various microorganisms has been reported (Japanese Published Unexamined Patent Application Nos. 116698/83 and 230094/88) but is inferior to chemical phosphorylation in terms of conversion rate and yield.

As an inosine-phosphorylating enzyme, inosine kinase (EC 2.7.1.73) is known but the crude active fraction derived from animal tissues or microorganisms is only reported [The Enzymes, Vol. IX, 54-56 (1973), Academic Press; Nucleosides and Nucleobases in Microorganisms, pp. 66, (1983), Academic Press]. The presence of a guanosine kinase activity which phosphorylates guanosine in E. coli is also suggested [J. Gen. Microbiol., 135, 1263-1273 (1989)]. However, the activity low and it is extremely difficult to purify the enzyme so that it is far beyond industrial utilization. In addition, physicochemical properties of the enzyme are not clarified. In any event, inosine-guanosine kinase is an enzyme that has been neither isolated nor purified.

An object of the present invention is to provide an inosine-guanosine kinase and also to provide a method for preparing 5'-nucleotides, inter alia, 5'-IMP and 5'-GMP, which have been widely utilized as seasoning agents industrially at low costs.

DISCLOSURE OF THE INVENTION

According to the present invention, there are provided an inosine-guanosine kinase derived from a microorganism belonging to the genus Escherichia which catalyzes the reaction of forming 5'-IMP from inosine and ATP or dATP and the reaction of forming 5'-GMP from guanosine and ATP or dATP, a process for producing the enzyme and a process for preparing 5'-nucleotides using the enzyme.

Hereafter the present invention is described in detail.

The inosine-guanosine kinase in accordance with the present invention can be obtained by culturing in a medium a microorganism belonging to the genus Escherichia having an ability to produce the inosine-guanosine kinase, producing and accumulating the inosine-guanosine kinase in cultured cells and recovering the inosine-guanosine kinase therefrom.

As the microorganism to be used, any of microorganisms may be obtainable from the natural world and constructed by genetic engineering so long as it belongs to the genus Escherichia and has an ability to produce the inosine-guanosine kinase.

Hereafter a method for obtaining the microorganism of the present invention constructed by genetic engineering and a method for producing the inosine-guanosine kinase using the microorganism are given below.

The inosine-guanosine kinase may be obtained by isolating chromosomal DNA from a microorganism belonging to the genus Escherichia, cloning a gene encoding the inosine-guanosine kinase to produce a bacterial strain having an enhanced inosine-guanosine kinase activity using genetic engineering and culturing the strain.

Isolation and cloning of the gene encoding the inosine-guanosine kinase derived from a strain belonging the genus Escherichia can be carried out as described below. That is, chromosomal DNA from strains of the genus Escherichia is isolated by a conventional method for isolation of DNA, for example, the phenol method [Biochim. Biophys. Acta, 72, 619-629 (1963)]. The resulting chromosomal DNA is cleaved with a suitable restriction enzyme, for example, BamHI, Sau3AI, BglII, etc. By inserting the fragment cleaved with the restriction enzyme into a vector DNA, a recombinant DNA in which the DNA fragment containing the gene encoding the inosine-guanosine kinase derived from a strain of the genus Escherichia has been inserted, can be obtained together variety of recombinant DNA mixtures. Among the recombinant DNA mixtures described above is the recombinant DNA comprising the DNA fragment containing the gene encoding the inosine-guanosine kinase. Using the recombinant DNA mixtures, a host microorganism is transformed according to the method of Cohen et al. [Proc. Natl. Acad. Sci. U.S.A., 69, 2110 (1979)].

As a source for the gene encoding the inosine-guanosine kinase, there is mentioned chromosomal DNA of a microorganism belonging to the genus Escherichia. Specific examples are Escherichia coli HM70 strain, Escherichia coli W3110 strain [Molecular Cloning, Cold Spring Harbor Laboratory (1982); ATCC 14948], etc.

As the vector harboring the DNA fragment containing the gene encoding the inosine-guanosine kinase inserted therein, any vector of phage vector, plasmid vector, etc. may be used as long as the vector is autonomously replicated in a strain belonging to the genus Escherichia. Preferred examples are pBR322 [Gene, 2, 95 (1977)], pUC19 [Gene, 33, 103 (1985)], pTrS30 [Doctoral Thesis by Tatsuya Nishi (1988), pp. 130, Tokyo University], etc.

Any host microorganism may be used as long as it belongs to the genus Escherichia and is capable of carrying a recombinant DNA obtained by inserting, into a vector, the gene encoding the inosine-guanosine kinase derived from a strain belonging to the genus Escherichia. Specific examples are *Escherichia coli* HM70 strain, *Escherichia coli* MC1000 strain [J. of Molecular Biology, 138, 179–207 (1980)], *Escherichia coli* DH1 strain [Molecular Cloning, 505, Cold Spring Harbor Laboratory (1982)], etc.

The gene may also be inserted into another bacterial species by subcloning the gene from the thus obtained recombinant DNA containing the gene encoding the inosine-guanosine kinase derived from a strain belonging to the genus Escherichia, by use of the host-vector system of the other species.

As the host-vector system, all known systems may be used. Examples include the host-vector systems of the genus Serratia, the genus Corynebacterium, the genus Brevibacterium the genus Pseudomonas, the genus Bacillus, etc.

*Escherichia coli* EM70 strain which is one of the sources for the gene encoding the inosine-guanosine kinase is a strain obtained by disrupting, on a genetic level, a part of the nucleoside-degrading activity of *Escherichia coli* SΦ609 strain [Molec. Gen. Genet., 143, 85–91 (1975)] obtained from National Genetics Research Institute through treatment with UV rays. The HM70 strain is used not only as a source for the gene but also as a host for cloning of the gene.

Selection of HM70 strain was made as follows. SΦ609 strain has an inosine-degrading activity and therefore, where the strain is allowed to grow on a plate medium supplemented with inosine, it degrades inosine into hypoxanthine and ribose. Furthermore, the SΦ609 strain can use ribose as a sugar source and thus, where it is allowed to grow on a sugar metabolism assay plate supplemented with inosine (MacCONKEY plate supplemented with inosine), it assimilates ribose so that red colonies are formed. Therefore, SΦ609 strain is smeared on inosine-supplemented MacCONKEY plate and UV rays are irradiated to such a degree that a killing rate becomes about 95%, whereby mutation is induced. The appearing white colonies are strains having a lowered ribose productivity, namely, strains having a decreased inosine-degrading activity. A strain having the lowest inosine-degrading activity is selected from the colonies and named HM70 strain.

SΦ609 strain and HM70 strain cannot grow on the minimum agar plate medium supplemented with hypoxanthine these strains lack the purine nucleotide biosynthesis pathway and the salvage pathway which produces 5'-IMP from hypoxanthine. However, HM70 strain having a decreased inosine-degrading activity which is about one fourth of that of SΦ609 strain can utilize inosine. Therefore, HM70 strain can grow even on inosine-supplemented minimum agar plate medium [plate medium prepared by dissolving 6 g of $Na_2HPO_4$, 3 g of $KH_2PO_4$, 0.5 g of NaCl, 1 g of $NH_4Cl$ and 15 g of agar in 1 liter of distilled water, adjusting pH to 7.4 with 1N NaOH, then sterilized by autoclaving and then adding a sterile solution of 2 ml of 1M $MgSO_4$, 10 ml of 20% glucose and 0.1 ml of 1M $CaCl_2$ (inosine was supplemented in a final concentration of 5 mM)], while SΦ609 strain cannot grow on that medium. However, this growth restoration results from a weak inosine guanosine kinase activity inherently possessed by HM70 strain and its growth rate is extremely low. When inosine-guanosine kinase structural gene ligated with a plasmid vector, is introduced into this HM70 strain, the inosine-guanosine kinase activity in the cells increases and growth on the inosine-supplemented minimum agar plate medium is accelerated. On the other hand, since the parent strain SΦ609 has a strong inosine-degrading activity, even though a recombinant DNA comprising the inosine-guanosine kinase gene and a plasmid vector is introduced into the parent strain, the parent strain cannot grow on inosine-supplemented minimum agar plate medium because of degradation of inosine in a medium.

From the thus obtained transformants, a strain having an activity which catalyzes the reaction of forming 5'-IMP from inosine and ATP or dATP and the reaction of form: 5'-GMP from guanosine and ATP or dATP is selected as follows.

The obtained transformants are treated with an organic solvent to afford membrane permeability thereto. Using the thus treated product as an enzyme source, the reaction of forming 5'-IMP from inosine and ATP or dATP or the reaction of forming 5'-GMP from guanosine and ATP or dATP is carried out. An amount of 5'-IMP or 5'-GMP produced is quantitatively determined by high performance liquid chromatography (HPLC). A strain which shows an increased amount of 5'-IMP or 5'-GMP produced is an inosine-guanosine kinase clone. Also where a transformant constructed by using HM70 strain as a host is inoculated on an inosine-supplemented minimum agar plate medium and kept at 30° C., a few colonies showing a fast growth appear in 2 to 3 days. Most of these strains showing a fast growth are inosine-guanosine kinase clones. From the obtained transformants, recombinant DNA molecules are isolated to obtain a recombinant DNA comprising the gene encoding the inosine-guanosine kinase derived from strain belonging to the genus Escherichia.

Examples of the strains in which inosine-guanosine kinase activity has been enhanced include *Escherichia coli* HM70/pBM2 carrying a recombinant DNA constructed by inserting into a vector a gene encoding the inosine-guanosine kinase derived from *Escherichia coli* HM70 strain, *Escherichia coli* DH1/pBM1 carrying a recombinant DNA constructed by inserting into a vector a gene encoding the inosine-guanosine kinase derived from *Escherichia coli* W3110, etc. *Escherichia coli* HM70/pBM2 and *Escherichia coli* DH1/pBM1 have respectively been deposited as *Escherichia coli* HM72 and *Escherichia coli* HM1 with the Fermentation Research Institute, Agency of Industrial Science & Technology, Japan, under the Budapest Treaty, as shown in Table 1.

TABLE 1

| Indication of Microorganism Recognition | FERM BP- | Date of Deposit |
|---|---|---|
| *Escherichia coli* HM72 | 3125 | October 6, 1990 |
| *Escherichia coli* HM1 | 2669 | December 1, 1989 |

These strains having an enhanced inosine-guanosine kinase activity are cultured in accordance with a convent method for culturing bacteria. That is, the microorganism may be cultured in a conventional medium containing carbon sources, nitrogen sources, inorganic compounds, amino acids, vitamins, etc. under aerobic conditions, while controlling temperature, pH, etc.

As the carbon sources used in a medium, carbohydrates such as glucose, fructose, sucrose, molasses, blackstrap molasses, starch hydrolyzate, etc. alcohols such as ethanol, glycerine, sorbitol, etc., organic acids such as pyruvic acid, lactic acid, acetic acid, etc. amino acids such as glycine, alanine, glutamic acid, aspartic acid, etc. can be used so long as the microorganism can assimilate them. A concentration of these carbon sources used is preferably 5 to 30%.

As the nitrogen sources, ammonia, ammonium salts of various inorganic and organic compounds such as ammonium chloride, ammonium sulfate, ammonium nitrate, ammonium carbonate, ammonium acetate, ammonium phosphate, etc. nitrogen-containing organic compounds such as urea, peptone, NZ amine, meat extract, yeast extract, corn steep liquor, casein hydrolyzate, fish meal or its digested products, etc. various amino acids such as glycine, glutamic acid, etc. can be used. A concentration of these nitrogen sources used is generally 0.1 to 10%.

As the inorganic compounds, potassium dihydrogen phosphate, dipotassium hydrogen phosphate, magnesium sulfate, magnesium phosphate, sodium chloride, ferrous sulfate, manganese sulfate, zinc sulfate, calcium carbonate, etc. can be used.

Where the microorganism to be used requires a specific nutrient such as amino acid, nucleic acid, vitamin, etc. for its growth, these substances are supplemented to a medium in a suitable amount.

Culturing is carried out under aerobic conditions such as shaking culture, agitation submerged culture, etc. A preferred temperature for culturing is generally 28° to 32° C. A period for culturing is generally 1 to 24 hours. A pH of medium is desirably kept neutral with ammonia, urea, a sodium hydroxide solution, etc.

After the completion of the culturing, the inosine-guanosine kinase may be isolated from the cultured cells in a conventional manner for collecting an enzyme, for example, as follows. Firstly the resulting cells are thoroughly washed and then ultrasonicated to give cell-free extract. After centrifugation, protamine sulfate is added to the resulting supernatant. The mixture is centrifuged to remove high molecular nucleic acid as precipitates. The supernatant is added to Sephadex G-50 followed by desalting through gel filtration. Subsequently, an anion exchange chromotography treatment using DEAE Sepharose and gel filtration through Sephacryl S-200 are carried out to give the purified product.

Components of each buffer in the specification refer to the following compounds.
HEPES: N-2-hydroxyethylpiperazine-N'-ethanesulfonic acid
PIPES: piperazine-N,N'-bis(2-ethanesulfonic acid)
TAPS: N-tris(hydroxymethyl)methyl-2-amino-1-propanesulfonic acid
CHES: cyclohexylaminoethanesulfonic acid The activity of the inosine-guanosine kinase obtained is determined as follows. A reaction solution (hereafter referred to as reaction solution a) having a composition of 100 mM HEPES buffer (pH 7.2), 10 mM $MgSO_4$, 50 mM KCl, 1 mM ATP and 1 mM inosine is brought into contact with the inosine-guanosine kinase in a concentration of about 10 µg protein/ml followed by reaction at 30° C. for about 30 minutes. During the course of reaction, a part of the reaction solution is subjected to sampling intermittently.

After the reaction solution is diluted to 1/20 with 0.2M $NaH_2PO_4$ (adjusted the pH to 2.6 with $H_3PO_4$) to stop the reaction, an amount of 5'-IMP in the stopped reaction solution is quantitatively determined by HPLC. Analysis by HPLC is made by using 0.2M $NaH_2PO_4$ (pH 2.6) at a flow rate of 1 ml/min. as an eluting solution and Asahipak GS-320H (manufactured by Asahi Chemical Co., Ltd.) as a column. Detection of components was made by the absorbance at UV absorbance at 254 nm as an index. Quantitative determination was made by comparing absorbancy with that of the standard.

Next, physicochemical properties of the obtained inosine-guanosine kinase are described below.

(1) Action

The enzyme has an action of forming ADP and 5'-IMP from ATP and inosine, an action of forming dADP and 5'-IMP from dATP and inosine, an action of forming ADP and 5'-GMP from ATP and guanosine, and an action of forming dADP and 5'-GMP from dATP and guanosine.

(2) Optimum pH

A reaction was carried out at 30° C. for 20 minutes in a manner similar to the method for determination of inosine-guanosine kinase activity described above, except that PIPES (pH 6.6–7.1), HEPES (pH 6.9–8.3), TAPS (pH 7.9–8.8) and CHES (pH 8.7–10.1) were replaced for the buffer component (100 mM) in the composition of reaction solution a. As the result, the optimum pH was 6.9–8.2.

(3) pH Stability

This enzyme is treated at 4° C. for 16 hours in an aqueous solution containing 50 mM buffer (CHES; pH 10.0–9.0), TAPS; pH 8.2, HEPES; pH 8.3–7.3 or PIPES; pH 6.6) and 5 mM β-mercaptoethanol under both conditions in the absence of KCl and in the presence of 250 mM KCl. After the treatment, the activity is determined. Where treated in a pH range of 6.6 to 9.0, the treated enzyme maintains the residual activity of 90% or more than the activity of intact standard enzyme and stably keeps its activity in a pH range of 6.6 to 9.0. The addition of KCl accelerates storage stability.

(4) Optimum Temperature

In the method for determination of inosine-guanosine kinase activity described above, the activity is determined by varying the temperature of 0° to 50° C. and 31° to 41° C. The optimum temperature is 25° to 40° C.

(5) Temperature Stability

A reaction solution composed of 20% glycerol, 50 mM Tris-hydrochloride buffer (pH 8), 5 mM β-mercaptoethanol and 100 mM NaCl is contacted with inosine-guanosine kinase in a concentration of about 10 µg protein/ml and treated at a temperature of 26° to 50° C. for 15 minutes to determine the residual activity at each temperature. As the result, since treatment at 40° C. or lower inactivates the enzyme by only 20% or less, the enzyme is stable up to 40° C. In contrast, the activity is rapidly lost by treatment at 50° C.

(6) Substrate Specificity

In the method for determination of inosine-guanosine kinase activity described above, a reaction is carried out at 30° C. by changing the concentration of KCl to 300 mM in the composition of reaction solution a and adding various neutralized phosphate sources to the reaction solution instead of ATP in a final concentration of 5 mM. As shown in FIG. 1, the reaction proceeds when using ATP or dATP as good substrate for phosphate-donor. Further in the case of uridine triphosphate (UTP), the reaction proceeds a little bit. However, adenosine diphosphate (ADP), adenosine monophosphate (5'-AMP), guanosine triphosphate (GTP), orotic acid monophosphate (5'-OMP), cytidine monophosphate (5'-CMP), p-nitrophenyl phosphate (PNPP), acetylphosphoric acid, tripolyphosphoric acid, tetrapolyphosphoric acid, pyrophosphoric acid and phosphoric acid could not be phosphate-donors. This indicates that the enzyme is classified in an enzyme group called a kinase and clearly distinguished from enzymes which govern transphosphorylation used in Japanese Published Unexamined Patent Application Nos. 119898/83 and 230094/88, etc., namely, nucleoside phosphotransferase (EC 2.7.1.77). Where ATP or dATP is used as phosphate-donor, inosine and guanosine are preferred as phosphate-acceptor.

(7) Inhibitor

In the method for determination of inosine-guanosine kinase activity described above, the activity is determined by reacting at 30° C. for 30 minutes except that the concentration of KCl is changed to 300 mM and 1 mM metal salt is added to the composition of reaction solution a. The activity is determined as a standard when no metal salt is added. The results are shown in Table 2. The enzyme is inhibited by metal ions such as $Co^{2+}$, $Cu^{2+}$, $Zn^{2+}$, etc.

TABLE 2

| Metal Salt (1 mM) | Relative Activity (%) |
|---|---|
| None | 100 |
| $FeCl_2$ | 112 |
| $FeCl_3$ | 131 |
| $CaCl_2$ | 107 |
| $CoCl_2$ | 32 |
| $CuCl_2$ | 1 |
| $MnCl_2$ | 134 |
| $BaCl_2$ | 116 |
| $ZnSO_4$ | 5 |
| $Zn(CH_3COO)_2$ | 5 |
| NaCl | 104 |
| NaF | 96 |

(8) Activation

In the method for determination of inosine-guanosine kinase activity described above, a reaction is carried out by changing the buffer to Tris-hydrochloride buffer (pH 8.0), and varying the concentration of KCl in the composition of reaction solution a. The results are shown in FIG. 2. Where 100 mM NaCl is added instead of KCl, no reaction proceeds. This reveals that the enzyme requires $K^+$ for activation. Next, activation is examined in the system where the concentration of KCl is changed to 300 mM in the composition of reaction solution a, by adding various divalent or trivalent metal ion salts instead of $MgSO_4$. As shown in Table 3, $Mg^{2+}$ and $Mn^{2+}$ exhibit an activating action. It is thus revealed that this enzyme requires one of two combinations: one is $K^+$ and $Mg^{2+}$ and the other is $K^+$ and $Mn^{2+}$.

TABLE 3

| Metal Salt (10 mM) | Produced IMP (mM) |
|---|---|
| None | 0 |
| $FeCl_2$ | 0 |
| $FeCl_3$ | 0 |
| $CaCl_2$ | 0 |
| $CoCl_2$ | 0.01 |
| $CuCl_2$ | 0 |
| $MnCl_2$ | 0.51 |
| $BaCl_2$ | 0 |
| $ZnSO_4$ | 0 |
| $Zn(CH_3COO)_2$ | 0 |
| $MgCl_2$ | 0.60 |
| $MnSO_4$ | 0.64 |
| $MgSO_4$ | 0.68 |

(9) Km Value

Km value in the reaction solution composed of 2 mM ATP, 10 mM $MgSO_4$, 300 mM KCl and 0.1M HEPES buffer (pH 7.2) was 2.1 mM for inosine and 6.1 µM for guanosine.

(10) Amino Acid Sequence and Nucleotide Sequence

Nucleotide sequence of the structural gene coding for this enzyme was determined by the dideoxy chain terminator method [Science, 214, 1205-1210 (1981), Gene, 19, 269-276 (1982)] and its amino acid sequence was deduced from the nucleotide sequence. The amino acid sequence and the nucleotide sequence are shown in Tables 4 and 5, respectively.

TABLE 4

MetLysPheProGlyLysArgLysSerLysHisTyrPheProValAsnAlaArgAspPro
LeuLeuGlnGlnPheGlnProGluAsnGluThrSerAlaAlaTrpValValGlyIleAsp
GlnThrLeuValAspIleGluAlaLysValAspAspGluPheIleGluArgTyrGlyLeu
SerAlaGlyHisSerLeuValIleGluAspAspValAlaGluAlaLeuTyrGlnGluLeu
LysGlnLysAsnLeuIleThrHisGlnPheAlaGlyGlyThrIleGlyAsnThrMetHis
AsnTyrSerValLeuAlaAspAspArgSerValLeuLeuGlyValMetCysSerAsnIle
GluIleGlySerTyrAlaTyrArgTyrLeuCysAsnThrSerSerArgThrAspLeuAsn
TyrLeuGlnGlyValAspGlyProIleGlyArgCysPheThrLeuIleGlyGluSerGly
GluArgThrPheAlaIleSerProGlyHisMetAsnGlnLeuArgAlaGluSerIlePro
GluAspValIleAlaGlyAlaSerAlaLeuValLeuThrSerTyrLeuValArgCysLys
ProGlyGluProMetProGluAlaThrMetLysAlaIleGluTyrAlaLysLysTyrAsn
ValProValValLeuThrLeuGlyThrLysPheValIleAlaGluAsnProGlnTrpTrp
GlnGlnPheLeuLysAspHisValSerIleLeuAlaMetAsnGluAspGluAlaGluAla
LeuThrGlyGluSerAspProLeuLeuAlaSerAspLysAlaLeuAspTrpValAspLeu
ValLeuCysThrAlaGlyProIleGlyLeuTyrMetAlaGlyPheThrGluAspGluAla
LysArgLysThrGlnHisProLeuLeuProGlyAlaIleAlaGluPheAsnGlnTyrGlu
PheSerArgAlaMetArgHisLysAspCysGlnAsnProLeuArgValTyrSerHisIle
AlaProTyrMetGlyGlyProGluLysIleMetAsnThrAsnGlyAlaGlyAspGlyAla
LeuAlaAlaLeuLeuHisAspIleThrAlaAsnSerTyrHisArgSerAsnValProAsn
SerSerLysHisLysPheThrTrpLeuThrTyrSerSerLeuAlaGlnValCysLysTyr
AlaAsnArgValSerTyrGlnValLeuAsnGlnHisSerProArgLeuThrArgGlyLeu
ProGluArgGluAspSerLeuGluGluSerTyrTrpAspArg

TABLE 5

| 1 | ATGAAATTTC | CCGGTAAACG | TAAATCCAAA | CATTACTTCC | CCGTAAACGC |
| 51 | ACGCGATCCG | CTGCTTCAGC | AATTCCAGCC | AGAAAACGAA | ACCAGCGCTG |
| 101 | CCTGGGTAGT | GGGTATCGAT | CAAACGCTGG | TCGATATTGA | AGCGAAAGTG |
| 151 | GATGATGAAT | TTATTGAGCG | TTATGGATTA | AGCGCCGGGC | ATTCACTGGT |
| 201 | GATTGAGGAT | GATGTAGCCG | AAGCGCTTTA | TCAGGAACTA | AAACAGAAAA |
| 251 | ACCTGATTAC | CCATCAGTTT | GCGGGTGGCA | CCATTGGTAA | CACCATGCAC |

TABLE 5-continued

```
 301 AACTACTCGG TGCTCGCGGA CGACCGTTCG GTGCTGCTGG GCGTCATGTG
 351 CAGCAATATT GAAATTGGCA GTTATGCCTA TCGTTACCTG TGTAACACTT
 401 CCAGCCGTAC CGATCTTAAC TATCTACAAG GCGTGGATGG CCCGATTGGT
 451 CGTTGCTTTA CGCTGATTGG CGAGTCCGGG GAACGTACCT TTGCTATCAG
 501 TCCAGGCCAC ATGAACCAGC TGCGGGCTGA AAGCATTCCG GAAGATGTGA
 551 TTGCCGGAGC CTCGGCACTG GTTCTCACCT CATATCTGGT GCGTTGCAAG
 601 CCGGGTGAAC CCATGCCGGA AGCAACCATG AAAGCCATTG AGTACGCGAA
 651 GAAATATAAC GTACCGGTGG TGCTGACGCT GGGCACCAAG TTTGTCATTG
 701 CCGAGAATCC GCAGTGGTGG CAGCAATTCC TCAAAGATCA CGTCTCTATC
 751 CTTGCGATGA ACGAAGATGA AGCCGAAGCG TTGACCGGAG AAAGCGATCC
 801 GTTGTTGGCA TCTGACAAGG CGCTGGACTG GGTAGATCTG GTGCTGTGCA
 851 CCGCCGGGCC AATCGGCTTG TATATGGCGG GCTTTACCGA AGACGAAGCG
 901 AAACGTAAAA CCCAGCATCC GCTGCTGCCG GGCGCTATAG CGGAATTCAA
 951 CCAGTATGAG TTTAGCCGCG CCATGCGCCA CAAGGATTGC CAGAATCCGC
1001 TGCGTGTATA TTCGCACATT GCGCCGTACA TGGGCGGGCC GGAAAAAATC
1051 ATGAACACTA ATGGAGCGGG GGATGGCGCA TTGGCAGCGT TGCTGCATGA
1101 CATTACCGCC AACAGCTACC ATCGTAGCAA CGTACCAAAC TCCAGCAAAC
1151 ATAAATTCAC CTGGTTAACT TATTCATCGT TAGCGCAGGT GTGTAAATAT
1201 GCTAACCGTG TGAGCTATCA GGTACTGAAC CAGCATTCAC CTCGTTTAAC
1251 GCGCGGCTTG CCGGAGCGTG AAGACAGCCT GGAAGAGTCT TACTGGGATC
1301 GT
```

10 amino acids sequence of the enzyme at the N-terminal were determined using Amino Acid sequencer of Applied Biosystem Co., Ltd. The amino acid sequence coincided with the amino acid sequence (Table 4) deduced from the nucleotide sequence shown in Table 5. Methionine which is the first amino acid of this enzyme is not cut out. Furthermore, C-terminal peptide is isolated and collected from peptide groups obtained by digesting the enzyme with lysyl endopeptidase and amino acid sequence of the C-terminal peptide was determined by the method described above. The amino acid sequence coincided with the C-terminal amino acid sequence shown in Table 4. The foregoing reveals that the amino acid sequence of this enzyme coincides with the amino acid sequence (Table 4) deduced from the nucleotide sequence shown in Table 5.

(11) Molecular Weight

Molecular weight deduced from the amino acid sequence is about 48400 daltons; according to measurement by SDS-polyacrylamide electrophoresis (manufactured by Biorad Co., Ltd., standard for low molecular weight, catalogue No. 161-0304 was used), molecular weight is about 43000 daltons.

The nucleotide sequence shown in Table 5 corresponds to the inosine-guanosine kinase represented by the amino acid sequence shown in Table 4. However, unless the inosine-guanosine kinase activity is lost, a strain carrying a recombinant DNA inserted with a gene obtained by modifying the nucleotide sequence may similarly be used as a strain having an increased inosine-guanosine kinase activity. Even in mutated enzyme produced by modifying guanine at the 1282nd position and its subsequent nucleotide sequence as shown in Table 6, its inosine-guanosine kinase activity is exhibited.

TABLE 6

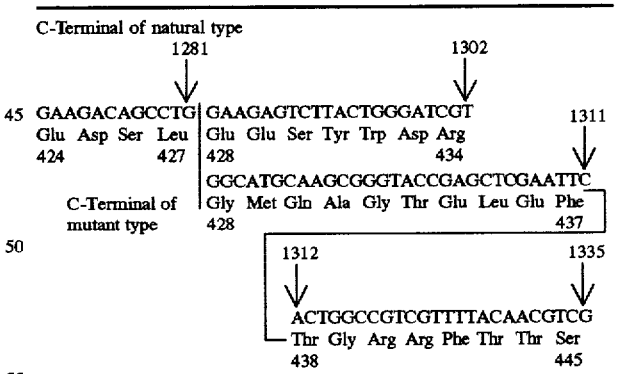

Next, mention may be made of process for producing 5'-nucleotides using the enzyme which catalyzes the reaction of forming 5'-nucleotides from nucleosides and ATP or dATP.

5'-nucleotides can be obtained by contacting nucleosides with ATP or dATP in an aqueous medium in the presence of an enzyme source having the enzyme activity which catalyzes the reaction of forming 5'-nucleotides from nucleosides and ATP or dATP.

As the nucleoside, inosine or guanosine is mentioned. As the 5'-nucleotides, 5'-IMP or 5'-GMP is mentioned.

As the enzyme source, inosine-guanosine kinase, bacterial cells having an ability to produce the enzyme, bacterial cells carrying a recombinant DNA obtained by inserting into a vector a DNA fragment containing a gene encoding the enzyme involved in the reaction of forming 5'-nucleotides from nucleosides and ATP or dATP, a culture thereof or treated matters thereof, etc. may be used.

As the treated matters, a concentrate of the culture or a dried culture, a culture treated with surfactant and/or organic solvent or lytic enzyme, bacterial cells obtained by centrifuging the culture, dried bacterial cells, acetone-treated cells, cells treated with surfactants and/or organic solvents, lytic enzyme-treated cells, immobilized bacterial cells or enzyme preparation extracted from bacterial cells, etc. may be used.

As the inosine and guanosine to be used in the reaction, any of purified or crude products, fermentation broth or cell-free supernatant of inosine and guanosine can be used for the reaction so long as they do not interfere the reaction of forming 5'-nucleotides. The concentration of nucleosides is in the range of from 10 to 80 g/l.

As the phosphate donor, there are ATP or dATP. Any of purified and crude ATP and dATP or materials containing ATP or dATP may be used as ATP or dATP source so long as they do not contain any substance that interferes with the reaction.

Since ATP and dATP are expensive, it is advantageous to add a microorganism having an ATP regenerating activity (Japanese Published Unexamination Patent Application No. 74595/86) to the reaction system, and to synthesize ATP from glucose and inorganic phosphoric acid.

In this case, an ATP precursor, an ATP regeneration energy donor, a phosphate donor and a microorganism having an ATP biosynthetic activity are allowed to exist in the reaction solution, instead of ATP. Where the reaction system coupled with the ATP regeneration system is used, it is sufficient to use ATP in a catalytic amount (1.0 g/l or less). Where a necessary amount is supplied and brought into the reaction system from bacteria or a culture, it is unnecessary to particularly supplement ATP. Examples of the strains having an ATP regenerating activity are *Brevibacterium ammoniagenes* KY13761 strain [Agric. Biol. Chem., 42, 399–405 (1978)], *Brevibacterium ammoniagenes* ATCC 21477 strain, etc.

*Brevibacterium ammoniagenes* KY13761 produce inosine by fermentation. Therefore, when inosine fermentation broth (containing cells) obtained by culturing this KY13761 strain, is used as a source of nucleoside and as a source of ATP regeneration, inosine in the fermentation broth can directly be phosphorylated without requiring purification of inosine so that an efficient process for producing 5'-IMP can be provided in a less expensive way.

The reaction for forming 5'-nucleotides from inosine or guanosine, and ATP or dATP is carried out at a temperature of 20° to 40° C. for 1 to 48 hours while adjusting pH to 6–8, preferably by adding a surfactant and/or an organic solvent. As the surfactant useful for treating the bacterial cells and for the reaction, there may be used surfactants including cationic surfactants such as polyoxyethylene stearylamine (e.g., Nymeen S-215, manufactured by Nippon Oil and Fats, Co., Ltd.; hereafter the same shall be used unless otherwise indicated), cetyltrimethylammonium bromide, cation FB, cation F2-40E, etc.; anionic surfactants such as sodium oleylamide sulfate, Newrex TAB, Rapizole 80, etc.; amphoteric surfactants such as polyoxyethylene sorbitan monostearate (e.g., Nonion ST221), etc.; tertiary amine PB, hexadecyldimethylamine, etc.; any other surfactants may be used so long as they accelerate the reaction of forming 5'-nucleotides from nucleosides and ATP or dATP. These surfactants may be used generally in a concentration of 0.1 to 50 mg/ml, preferably 1 to 20 mg/ml.

As the organic solvent, toluene, xylene, aliphatic alcohols, benzene, ethyl acetate may be used. The organic solvent may be used generally in a concentration of 0.1 to 50 μl/ml, preferably 1 to 20 μl/ml.

After completion of the reaction, 5'-nucleotides produced and accumulated in the reaction solution are obtained in a conventional manner using ion exchange resin, etc.

BEST MODE FOR PRACTISING THE INVENTION

Figure 1:
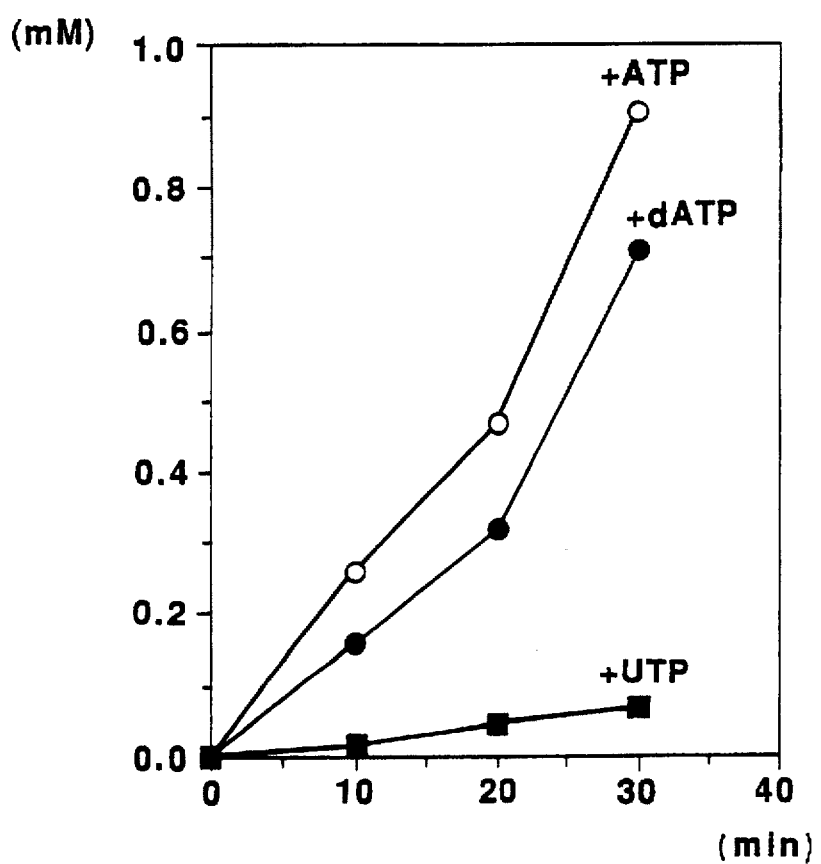
FIG. 1 relates to substrate specificity for inosine-guanosine kinase, wherein the ordinate represents an amount of 5'-IMP produced and the abscissa represents time.
Figure 2:
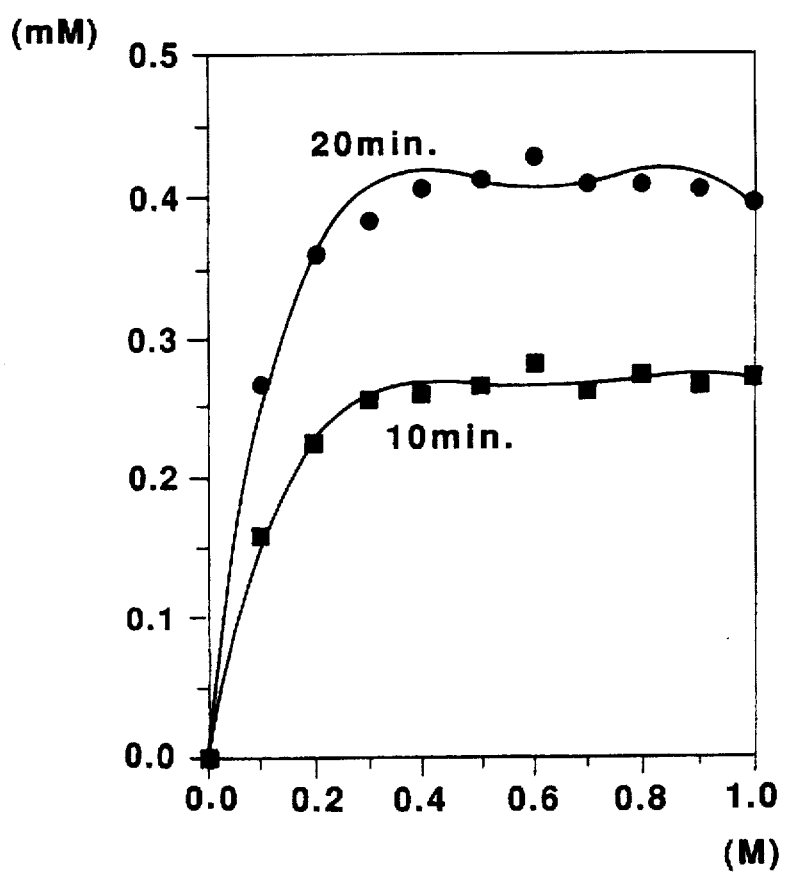
FIG. 2 relates to KCl dependency of inosine-guanosine kinase, wherein the ordinate represents an amount of 5'-IMP produced and the abscissa represents an amount of KCl added.

In the following examples, reagents and vectors used in genetic engineering experiments are all manufactured by Takara Shuzo Co., Ltd. Other reagents are those manufactured by Nakarai Tesque Co., Ltd.

Example 1

(1) Isolation of DNA

*Escherichia coli* HM70 strain was inoculated into LB liquid medium [1% trypton, 0.5% yeast extract and 1% sodium chloride (pH 7.5)] followed by culturing at 37° C. overnight. After 15 g of the cultured cells was suspended in 120 ml of 20 mM Tris-hydrochloride buffer (pH 7.5) containing 2 mM EDTA, 15 ml of lysozyme solution (20 mg/ml lysozyme was dissolved in 20 mM Tris-hydrochloride buffer (pH 7.5) containing 2 mM EDTA) was added to the suspension. The mixture was allowed to stand at 30° C. for an hour. Then 15 ml of 20% sodium laurylsulfate was added thereto and the mixture was slowly stirred. Next, 150 ml of phenol saturated with 10 mM Tris-hydrochloride buffer containing 1 mM EDTA was added to the solution followed by thoroughly stirring. The solution was centrifuged and 150 ml of the aqueous layer was fractionated. Such procedure for the phenol extraction was repeated 3 times. To 150 ml of the obtained aqueous layer were added 15 ml of 2.5M sodium acetate solution and further 300 ml of ethanol. The precipitated chromosomal DNA was wound up around a glass rod and dried. Then, chromosomal DNA was dissolved in 30 ml of 10 mM Tris-hydrochloride buffer containing 1 mM EDTA and 50 µg/ml ribonuclease was added to the solution. The mixture was allowed to stand at 37° C. for 30 minutes. After the same procedure for phenol extraction as described above was performed, 3 ml of 2.5M sodium acetate solution and 60 ml of ethanol were added to the aqueous layer followed by standing at −20° C. for 16 hours. After centrifugation, the obtained pellet was washed with 70% ethanol solution and dried to give purified chromosomal DNA. The chromosomal DNA was suspended in 10 mM Tris-hydrochloride buffer containing 1 mM EDTA.

(2) Preparation of Recombinant DNA

Sau3AI was added to the suspension containing 1 µg of chromosomal DNA obtained in (1) to perform partial digestion. Separately, BamHI was added to 20 µl of a solution containing 1 µg of vector pUC19 for digestion. Then, 2 µl of 1M Tris-hydrochloride buffer (pH 8.0) was added thereto and the mixture was treated with alkaline phosphatase at 65° C. for an hour. The digested chromosomal DNA and vector DNA described above were purified by the same procedures for phenol extraction and ethanol precipitation as in (1). After 100 ng of purified chromosomal DNA and 20 ng of purified vector DNA were suspended in a solution containing 66 mM Tris-hydrochloride buffer (pH 7.6), 66 mM magnesium chloride, 10 mM DTT and 0.1 mM ATP, 10 units of T4 ligase were added to the suspension. The mixture was allowed to stand at 14° C. for 16 hours for the purpose of ligating chromosomal DNA with vector DNA to obtain a recombinant DNA.

(3) Preparation of an *Escherichia coli* Strain with the Recombinant DNA Introduced Therein

*Escherichia coli* HM70 strain was inoculated in 50 ml of LB liquid medium followed by culturing at 37° C. for 4 hours. The bacteria harvested by centrifugation at 3000 rpm for 7 minutes were suspended at 0° C. in 20 ml of 50 mM calcium chloride solution. After the suspension was allowed to stand at 0° C. for 20 minutes, the cells were collected by the same centrifugation as described above and suspended at 0° C. in 40 ml of 50 mM calcium chloride solution. The suspension was mixed with the solution containing the recombinant DNA obtained in (2) and the mixture was allowed to stand at 0° C. for 10 minutes. After heat-treating at 42° C. for 90 seconds, the mixture was smeared on minimum agar plate medium containing 50 µg/ml ampicillin and 5 mm inosine. This plate medium was kept at 30° C. for 48 to 72 hours.

(4) Isolation of DNA Encoding Inosine-guanosine Kinase

Several colonies appeared on the plate medium described in (3) in 2 to 3 days. Each of the colonies was cultured at 30° C. overnight in LB liquid medium. A part of each culture was smeared on a minimum agar plate medium containing 50 µg/ml ampicillin and 5 mM inosine, which was kept at 30° C. for 36 to 48 hours. On the second day a colony which grew well, namely, a transformant carrying a recombinant DNA containing the inosine-guanosine kinase gene was selected. The transformant carrying a recombinant DNA containing the inosine-guanosine kinase gene was cultured in LB liquid medium at 30° C. overnight. After the cells were harvested, plasmid DNA was isolated by the method described in Maniatis et al. [Molecular Cloning (1982), Cold Spring Harbor Laboratory] and its nucleotide sequence was determined by the dideoxy method [Messing, J., Methods in Enzymology, 101], 20–78 (1983)]. The nucleotide sequence of the structural gene moiety of inosine-guanosine kinase is as shown in Table 5.

The thus obtained recombinant DNA containing the gene encoding inosine-guanosine kinase derived from *Escherichia coli* HM70 strain was named pBM2. A restriction enzyme map of pBM2 is shown in FIG. 3.

Figure 3:
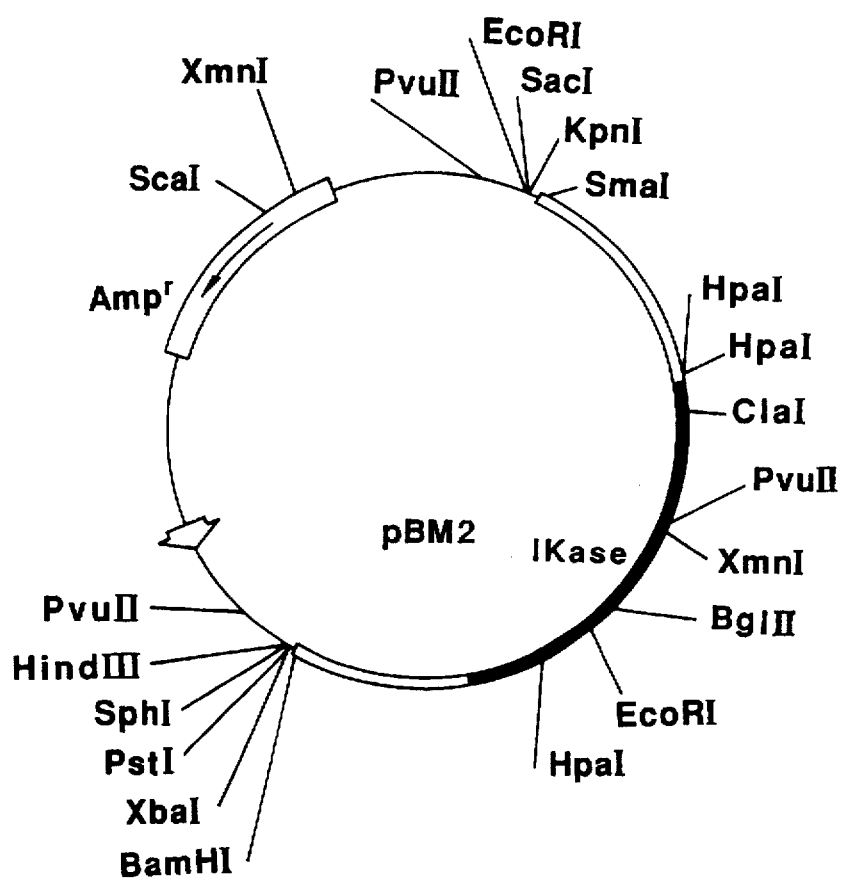
FIG. 3 is a restriction enzyme map of plasmid pBM2 containing a gene encoding inosine-guanosine kinase derived from *Escherichia coli* HM70 strain.

In FIG. 3, part indicated with black bold line is the structural gene encoding inosine-guanosine kinase derived from *Escherichia coli* HM70 strain. The direction of transcription of the gene is from ClaI site to BglII site in the figure.

(5) Construction of the Plasmid Which Highly Expresses Inosine-guanosine Kinase and its Introduction into a Microorganism The structural gene of inosine-guanosine kinase is ligated downstream of tryptophan promoter of *Escherichia coli*, whereby inosine-guanosine kinase can be expressed in high efficiency.

Figure 4:
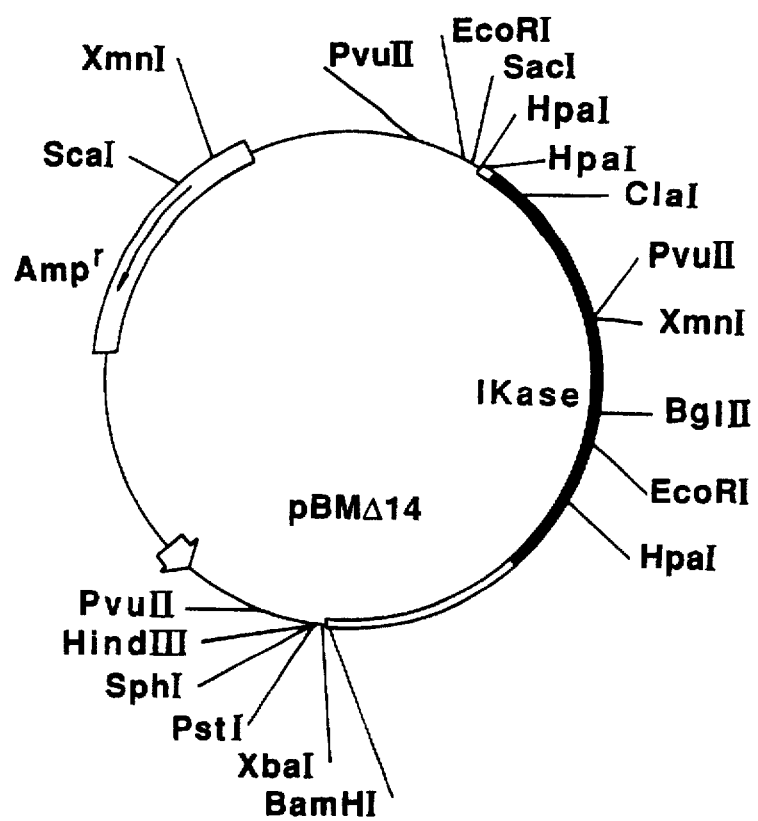
FIG. 4 is a restriction enzyme map of mutant plasmid pBM Δ14 in which deletion in the structural gene of inosine-guanosine kinase has occurred up to the 5' end.
Figure 5:
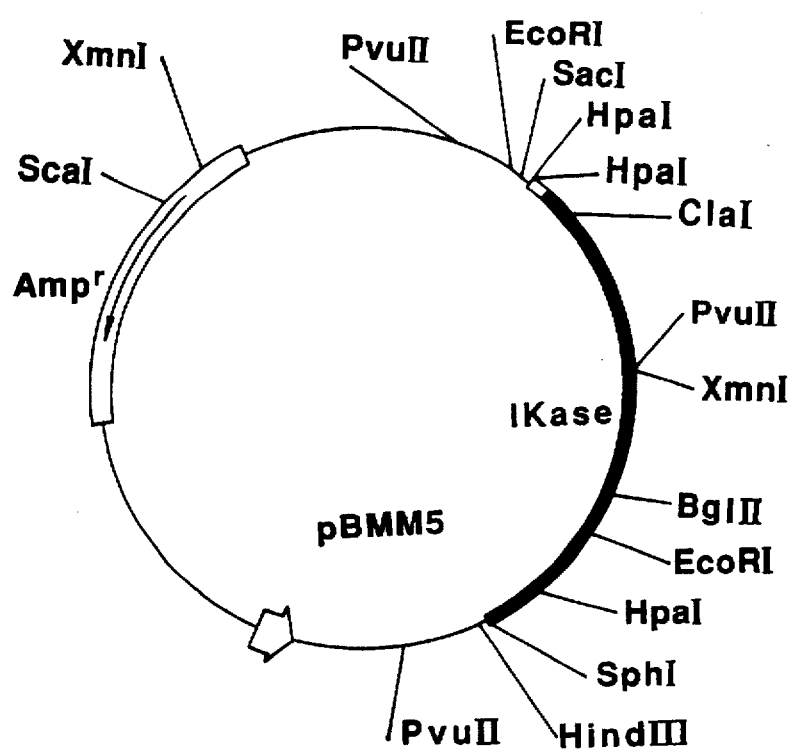
FIG. 5 is a restriction enzyme map of mutant plasmid pBMM5 in which deletion in the structural gene of inosine-guanosine kinase has occurred up to the 3' end.
Figure 6:
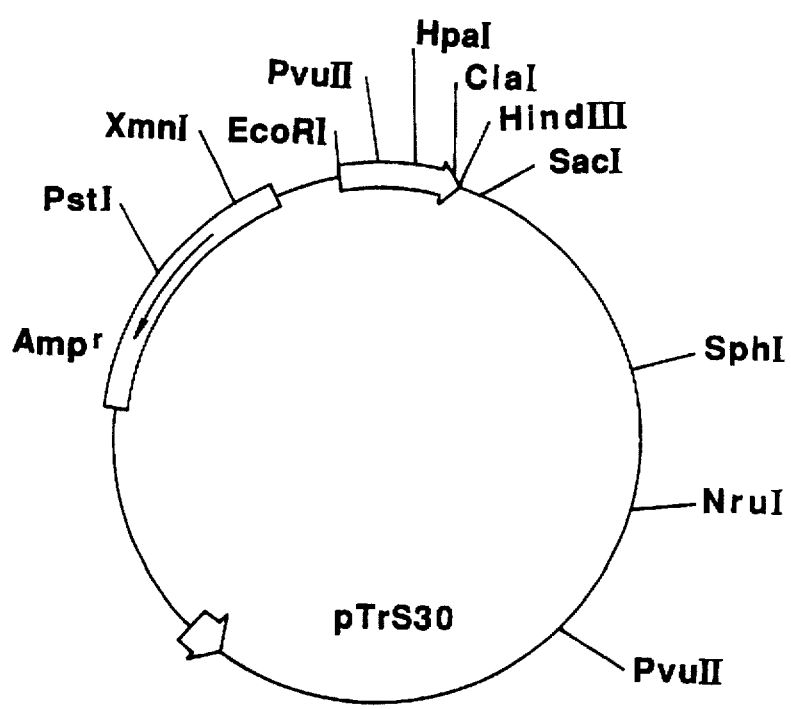
FIG. 6 is a restriction enzyme map of vector pTrS30.
Figure 7:
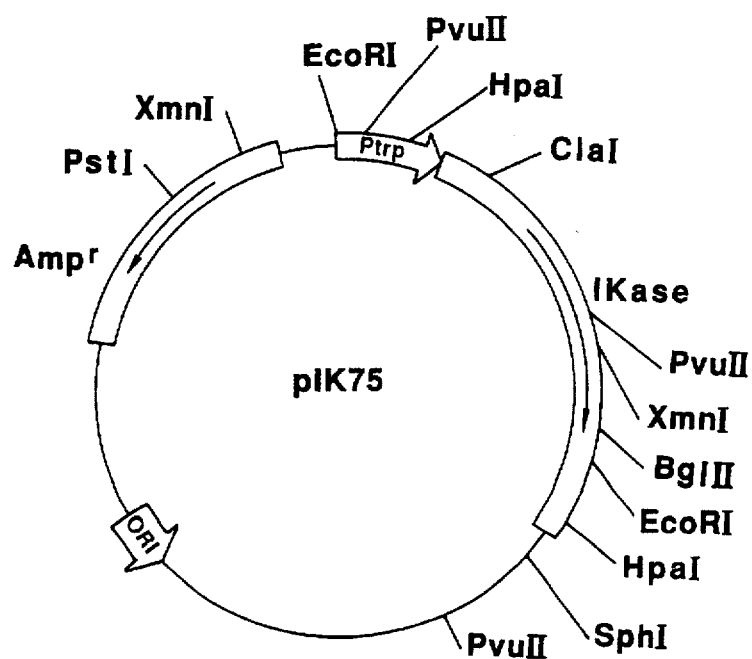
FIG. 7 is a restriction enzyme map of plasmid pIK75 which efficiently expresses inosine-guanosine kinase.
Figure 8:
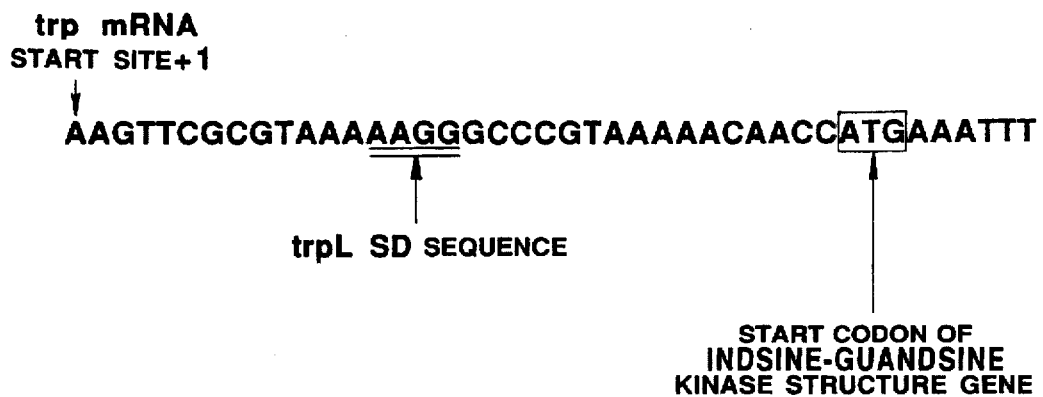
FIG. 8 shows a nucleotide sequence at the junction between tryptophan promoter and the structural gene of inosine-guanosine kinase.

According to Molecular Cloning (pp. 86–96), plasmid pBM2 obtained in (4) was purified. Using restriction enzymes SmaI (5 units) and KpnI (5 units), 10 µg of pBM2 was fully digested. The resulting digested product was treated with ExoIII nuclease to prepare a mutant in which gene located to the direction of the inserted fragment are deleted. Mutant plasmid pBMΔ14 (FIG. 4) in which the deletion had occurred up to 5' end of the inosine-guanosine kinase structural gene was selected. For construction of the deletion mutant, deletion kit for killo sequencing was used according to the brochure attached. This plasmid pBMΔ14 was digested with PstI and XbaI and a mutant in which a gene located to the direction of the inserted fragment was digested by ExoIII nuclease, was prepared in the same way. Thus, mutant plasmid pBMM5 (FIG. 5) in which the deletion had occurred up to 3' end of the inosine-guanosine kinase structural gene was obtained. After 10 µg of pBMM5 was digested with 10 units of restriction enzyme HindIII, the digested end was made to be a blunt end using the DNA blunting kit. Ethanol was added to collect the DNA having a blunt end as precipitates and this DNA was digested with restriction enzyme SacI. The digested product was isolated by agarose gel electrophoresis and a fragment containing the inosine-guanosine kinase structural gene was recovered from the gel (using DNA Prep manufactured by Asahi Glass Co., Ltd.) The recovered fragment was inserted into SacI-NruI site of vector pTrS30 (FIG. 6) to give plasmid pIK1. Then 10 µg of pIK1 was digested with 5 units of ClaI (ClaI site in the inosine-guanosine kinase structural gene does not undergo digestion since it is generally modified by methylation). After the digested product was recovered as precipitates by addition of ethanol, deletion was introduced at both of the digestion ends using nuclease BAL31. The deletion plasmid was recovered as precipitates by addition of ethanol followed by ligation treatment (ligation kit). The deletion plasmid was used for transformation of MC1000 strain. From the obtained transformants, various deletion plasmids were obtained. From these plasmids, plasmid pIK75 (FIG. 7) in which the inosine-guanosine kinase structural gene had been ligated right down stream of Shine-Dalgarno sequence derived from vector was selected. The nucleotide sequence at the junction between tryptophan promoter and the inosine-guanosine kinase structural gene is shown in FIG. 8. Genetic engineering techniques such as digestion with restriction enzymes, etc. used in this section were performed according to Molecular Cloning, unless otherwise indicated.

(6) Culture of a Highly Inosine-guanosine Kinase-expressed Microorganism

Where MC1000 strain carrying plasmid pIK75 obtained in (5) [hereafter referred to as MC1000(pIK75)] is cultured, high density culture method [Biotechnol. Bioeng., 17, 227–239 (1975)] is appropriate. MC1000(pIK75) strain was cultured by the high density culture method.

MC1000(pIK75) strain was inoculated into 500 ml of seed medium having the following composition followed by culturing at 30° C. for 16 hours.

Composition of seed medium: 3.5 g/l $KH_2PO_4$, 3.5 g/l $(NH_4)_2HPO_4$, 1.0 g/l $MgSO_4.7H_2O$, 5.0 g/l glucose, 5.0 g/l yeast extract, 3 ml/l trace element solution (sterilized at 120° C. for 30 minutes by steam)

Composition of trace element solution: 27 g/l $FeCl_3.6H_2O$, 2 g/l $ZnCl_2.4H_2O$, 2 g/l $CoCl_2.6H_2O$, 2 g/l $Na_2MoO_4.2H_2O$, 1 g/l $CaCl_2.2H_2O$, 1 g/l $CuCl_2$, 0.5 g/l $H_3BO_3$, 100 mL/l conc. HCl.

Next, 3 l of a fermentation medium (medium obtained by further adding 10 g of $KH_2PO_4.3H_2O$ and 5 g of $MgSO_4.7H_2O$ to 3 l of seed medium having the composition described above) was charged in a fermentation tank of 7.5 l volume followed by sterilization at 120° C. for 30 minutes with steam. After 150 ml of 50% (w/v) sterile glucose solution was added to the fermentation tank, 500 ml of the seed medium in which MC1000 (pIK75) had been cultured was added.

While adjusting the pH to 6.8 with 5.5M aqueous ammonia, culture was continued for 24 hours with agitation (6000 rpm) and aeration (3 l/min). In 4 to 6 hours after initiation of culture, a glucose concentration in the culture was reduced to 2.5% or less. From this point, 50% (w/v) glucose solution was continuously fed in the fermentation tank little by little to maintain the glucose concentration in the culture at 2 to 3%. (The culture was centrifuged and the cells recovered as precipitates were stored at −20° C. The cells were used in the following (7) and (9). Furthermore the medium after completion of the culture was frozen at −20° C. and thawed at 30° C. immediately before use in the following (10)).

(7) Purification of Inosine-guanosine Kinase

After 6 g of the −20° C.-stored cells which had been obtained in (6) was suspended in 24 ml of purification buffer [20% glycerol, 50 mM Tris-hydrochloride buffer (pH 8) and 5 mM β-mercaptoethanol], the suspension was disrupted with a homogenizer (manufactured by Brown Biotech Co., Ltd., glass bead diameter of 0.1 mm). The homogenate was centrifuged to give about 20 ml of the supernatant. Protamine sulfate was added to the supernatant in a final concentration of 0.4% followed by centrifugation. Thus high molecular nucleic acid components were removed as precipitates. The resulting supernatant was passed through Sephadex G-50 column which had been previously equilibrated with the purification buffer. The column was eluted with the purification buffer to give about 30 ml of desalted active fraction. After the fraction was passed through DEAE Sepharose column which had been previously equilibrated with the purification buffer, 60 ml of the purification buffer containing 0.1M NaCl was added thereto. Then the desired enzyme was eluted with 200 ml of the purification buffer having an NaCl linear density slope of 0.1M to 0.6M. From the active fractions eluted, 3 ml of the fraction having the highest enzyme concentration was collected. This active fraction was passed through Sephacryl S-200 column and eluted with the purification buffer containing 0.1M NaCl. By gel filtration, the active fraction was collected. Finally 10 ml of purified enzyme (1.4 μg protein/ml) was obtained. This purified enzyme was analyzed by SDS-polyacrylamide electrophoresis but no impurity was detected. The enzyme is stably stored at −20° C. in the purification buffer containing 0.1M NaCl.

(8) Culture of a Microorganism Capable of Regenerating ATP

*Brevibacterium ammoniagenes* KY13761 strain was cultured at 30° C. for 2 days on a seed agar medium plate prepared by adding 25 g/l agar to a seed medium having the composition described in Table 7. The obtained cells were inoculated into 30 ml of seed medium contained in an Erlenmeyer's flask of 250 ml volume followed by shaking culture at 30° C. for 24 hours.

The 30 ml of the resulting culture was inoculated into 3 l of seed medium having the composition described in Table 7, in a fermentation tank of 5 l volume. While adjusting pH to 6.8 with 5.5M aqueous ammonia, culture was continued for 24 hours with agitation at 600 rpm and aeration of 3 l/min.

300 ml of the obtained culture was inoculated into 3 l of fermentation medium having a composition described in Table 7, in a fermentation tank of 5 l volume. While adjusting pH to 6.8 with 5.5M aqueous ammonia, culture was continued at 32° C. for 42 hours with agitation at 600 rpm and aeration of 3 l/min. [The medium was centrifuged and the cells recovered as precipitates were stored at −20° C. The cells were used in the following (9). Furthermore the medium (containing about 30 g/l of inosine) after completion of the culture was directly frozen at −20° C. and thawed at 30° C. immediately before use in the following (10)].

TABLE 7

| Composition (g/l) | Seed Medium | Fermentation Medium |
|---|---|---|
| Glucose | 50 | 150 |
| $KH_2PO_4$ | 1 | 10 |
| $K_2HPO_4$ | 3 | 10 |
| $MgSO_4.7H_2O$ | 1 | 10 |
| $CaCl_2.2H_2O$ | 0.1 | 0.1 |
| $FeSO_4.7H_2O$ | 0.01 | 0.01 |
| $ZnSO_4.7H_2O$ | 0.001 | 0.001 |
| $MnSO_4.4-6H_2O$ | 0.004 | 0.004 |
| L-Cystein.HCl | 0.02 | 0.02 |
| Thiamine | 0.005 | 0.005 |
| Ca-D-pantothenate | 0.01 | 0.01 |
| Nicotinic aicd | none | 0.005 |
| Biotin | 30 μg/l | 30 μg/l |
| Urea | 5 | 2 |
| $(NH_4)_2SO_4$ | 5 | none |
| Meat extract | none | 10 |
| Polypeptone | 10 | none |
| Yeast extract | 10 | none |
| Adenine | 0.3 | 0.2 |
| pH | 7.2 | 8.3 |

[used after steam sterilization (120° C., 30 minutes)]

(9) Production of 5'-nucleotides from Nucleosides by Resting Cell Reaction

While maintaining at 32° C. by strongly stirring 20 ml of a solution having composition shown in Table 8, reaction was carried out for 24 hours, while keeping pH at 7.2 using 4N NaOH. A small amount of the reaction mixture was subjected to sampling intermittently to determine concentrations of phosphoric acid, inosine and 5'-IMP in the mixture. For quantitative assay for phosphoric acid, Phospho B-test WAKO (manufactured by Wako Pure Chemical Industry Co., Ltd.) was used and a difference between measurement data every time and initial addition was complemented by adding monopotassium phosphate. Concentrations of inosine and 5'-IMP were quantitatively determined by HPLC according to a modification of the method described hereinbefore. About 100 g/l of 5'-IMP (calculated as disodium 7.5 hydrate) was produced from about 50 g/l of initial inosine 24 hours after the reaction. In this case, a molar conversion rate was 90% or more. When guanosine was added instead of inosine, 5'-GMP was produced in a molar conversion rate of 90% or more with similar time course.

TABLE 8

| Composition of reaction solution | |
|---|---|
| KY13761 strain | 200 g wet cell weight/l |
| MC1000 (pIK75) strain | 20 g wet cell weight/l |
| Inosine | 50 g/l |
| Monopotassium phosphate | 20 g/l |
| Glucose | 30 g/l |
| Magnesium sulfate | 5 g/l |
| Xylene | 10 ml/l |
| Nymeen S-215 | 4 g/l |
| Phytic acid | 5 g/l |

(10) Production of 5'-IMP from Inosine Using Inosine Fermentation Medium

After completion of fermentation, about 30 g/l of inosine was accumulated in the medium obained in (8) above. As indicated in Table 9, 20 ml of a reaction mixture containing this medium was prepared. In a manner similar to (9), while keeping at 32° C. with vigorously stirring and also keeping pH at 7.2 with 4N NaOH, a reaction was carried out for 13 hours. During the course of reaction, monopotassium phosphate was added as in (9). From 23.5 g/l of initial inosine, 46 g/l of 5'-IMP was produced and accumulated. Also in this case, its molar conversion rate was 90% or more, as in (9).

TABLE 9

| Composition of reaction solution | |
|---|---|
| Inosine culture broth (containing KY13761 cells) | 15.7 ml |
| MC1000(pIK75) culture broth | 1.82 ml |
| Monopotassium phosphate | 0.4 g |
| Glucose | 0.7 g |
| Magnesium sulfate | 0.1 g |
| Xylene | 0.2 ml |
| Nymeen S-215 | 80 mg |
| Phytic acid | 100 mg |
| (Distilled water is added to the foregoing components until 20 ml). | |

Example 2

(1) Isolation of DNA

Purified chromosomal DNA was obtained in a manner similar to Example 1 (1) except for using *Escherichia coli* W3110 strain in place of *Escherichia coli* HM70 strain. The chromosomal DNA was suspended in 10 mM Tris-hydrochloride buffer containing 1 mM EDTA.

(2) Preparation of Recombinant DNA

A recombinant DNA was obtained in a manner similar to Example 1 (2) except for using the suspension containing 1 µg of chromosomal DNA obtained in Example 2 (1) in place of the suspension obtained in Example 1 (1).

(3) Preparation of an *Escherichia coli* Strain with the Recombinant DNA Introduced Therein

*Escherichia coli* DH1 strain was inoculated into 50 ml of LB liquid medium followed by culturing at 37° C. for 4 hours. The bacteria harvested by centrifugation at 3000 rpm for 7 minutes were suspended at 0° C. in 20 ml of 50 mM calcium chloride solution. The suspension was allowed to stand at 0° C. for 20 minutes, the cells were collected by the same centrifugation as described above and suspended at 0° C. in 40 ml of 50 mM calcium chloride solution. The suspension was mixed with the solution containing recombinant DNA obtained in Example 2 (2) and the mixture was allowed to stand at 0° C. for 10 minutes. After heat-treating at 42 C. for 90 seconds, the mixture was smeared on LB agar medium plate (LB liquid medium containing 1.5% agar) supplemented with 50 µg/ml of ampicillin, 0.1 mM isopropylthiogalactoside (IPTG) and 0.004% of 5-bromo-4-chloro-3-indoly-β-D-galactopyranoside.

Several colonies appeared on the plate medium in 2 to 3 days. Each of the colonies was cultured at 30° C. overnight in 10 ml of LB liquid medium and the cells were isolated by centrifugation. These isolated cells were stored at −20° C. and their inosine guanosine-kinase activity was determined in order by the method shown below.

(4) Isolation of DNA Encoding Inosine-guanosine Kinase

*Escherichia coli* cells containing the recombinant DNA collected in Example 2 (3) were suspended (cell concentration was 100 g wet cell weight/ml) in 100 mM Tris-hydrochloride buffer (pH 8.0) containing 10 mM ATP, 10 mM inosine and 5 mM magnesium sulfate. Xylene was added to the suspension in a concentration of 10 ml/l. After thoroughly stirring, the mixture was allowed to stand at 30° C. for an hour. The reaction solution was analyzed by HPLC and an amount of 5'-IMP in the reaction solution was quantitatively determined. Almost all transformants did not produce 5'-IMP but 5'-IMP-producing bacteria were obtained in a proportion of 1 out of 50,000 samples. The thus obtained 5'-IMP-producing bacteria are transformants carrying a recombinant DNA containing inosine guanosine-kinase gene.

The obtained transformants were cultured at 30° C. overnight in LB liquid medium and the cells were collected. Thereafter plasmid DNA was isolated by the method described in Molecular cloning and its nucleotide sequence was determined by the dideoxy method. The nucleotide sequence of the structural gene moiety of inosine-guanosine kinase is as shown in Table 5.

Figure 9:
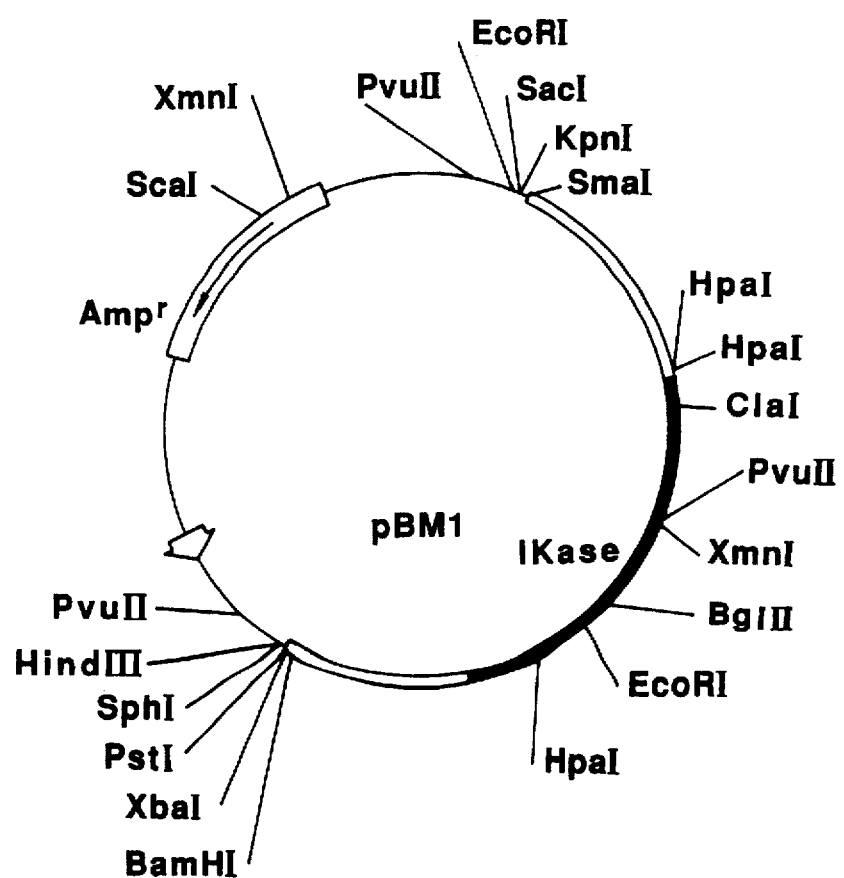
FIG. 9 is a restriction enzyme map of plasmid pBM1 containing a gene encoding inosine-guanosine kinase derived from *Escherichia coli* W3110 strain.

The thus obtained recombinant DNA containing the gene encoding inosine-guanosine kinase derived from *Escherichia coli* W3110 strain was named pBM1. A restriction enzyme map of PBM1 is shown in FIG. 9.

(5) Preparation of 5'-IMP

Transformant *Escherichia coli* HM1 (FERM BP-2669) transformed with recombinant DNA pBM1 obtained in Example 2 (4) was cultured at 30° C. for 16 hours in 400 ml of LB liquid medium (containing 50 µg/ml of ampicillin). The medium was then centrifuged to give the cells. For control, the culture cells of *Escherichia coli* DH1/pUC19 containing vector pUC19 alone were obtained in a manner similar to the above. After 20 ml of a solution of Table 10 containing the obtained cells was reacted at 30° C. for an hour, an amount of 5'-IMP produced in the solution was quantitatively determined by HPLC and found to be 5 mg. Where the cells from the strain carrying the vector for control was used, no 5'-IMP was detected in the solution.

TABLE 10

| Composition of reaction solution | |
| --- | --- |
| Cell | 100 g wet cell weight/l |
| Inosine | 10 mM |
| ATP | 10 mM |
| Tris-hydrochloride buffer (pH 8.0) | 100 mM |
| Magnesium sulfate | 5 mM |
| Xylene | 10 ml/l |

(6) Preparation of 5'-GMP

Transformant *Escherichia coli* HM1 carrying recombinant DNA pBM1 obtained in Example 2 (4) was cultured at 30° C. for 16 hours in 400 ml of LB liquid medium (containing 50 µg/ml ampicillin). The medium was then centrifuged to give the cells. For control, the culture cells of *Escherichia coli* DH1/pUC19 containing vector pUC19 alone were obtained in a manner similar to the above. After 20 ml of a solution of Table 11 containing the obtained cells was incubated at 30° C. for an hour, an amount of 5'-GMP produced in the solution was quantitatively determined by HPLC and found to be 2 mg. Where the cell of the strain carrying the vector for control was used, no 5'-GMP was detected in the solution.

TABLE 11

| Composition of reaction solution | |
| --- | --- |
| Cell | 100 g wet all weight/l |
| Guanosine | 10 mM |
| ATP | 10 mM |
| Tris-hydrochloride buffer (pH 8.0) | 100 mM |
| Magnesium sulfate | 5 mM |
| Xylene | 10 ml/l |

(7) Amplification of Activity by Genetic Engineering

By ligating SD sequence and strong promoter sequence upstream the inosine-guanosine kinase structural gene by genetic engineering technique, expression of inosine-guanosine kinase can be amplified. The amplification can be made as follows.

After 20 µl of a solution containing 1 µg of plasmid pBM1 obtained in Example 2 (4) was fully digested with 10 units of BamHI, 10 units of SacI and 10 units of ScaI, 2.8 kb fragment containing the inosine-guanosine kinase structural gene was isolated and purified by agarose gel electrophoresis (Molecular Cloning). After the purified fragment was digested with BAL31 nuclease at 37° C. for 10 minutes, phenol extraction and ethanol precipitation were performed to obtain a DNA fragment having deletion at the end. Separately, 10 units of SmaI was added to 20 µl of a solution containing 1 µg of vector pUC19 for full digestion. Then 2 µl of 1M Tris-hydrochloride buffer (pH 8.0) was added and further 5 units of alkaline phosphatase was added thereto followed by reaction at 65° C. for an hour. The purified inosine-guanosine kinase-containing DNA fragment (100 ng) and 20 ng of alkaline phosphatase-treated vector DNA were suspended in a solution containing 66 mM Tris-hydrochloride buffer (pH 7.6), 66 mM magnesium chloride, 10 mM DTT and 0.1 mM ATP. To the suspension were added 10 units of T4 ligase. The mixture was reacted at 14° C. for 16 hours to ligate both DNAs, thereby to obtain a recombinant DNA. The recombinant DNA was introduced into *Escherichia coli* DH1 strain in a manner similar to Example 2 (3). The obtained transformants were cultured in a manner similar to Example 2 (3). The inosine-guanosine kinase activity was determined in a manner similar to Example 2 (4) and a strain having a high 5'-IMP productivity was selected. The strain was named *Escherichia coli* BM100 strain. In recombinant plasmid carried by *Escherichia coli* BM100 strain, lactose promoter sequence was ligated upstream the inosine-guanosine kinase structural gene in a correct direction.

(8) Preparation of 5'-IMP

*Escherichia coli* BM100 strain was cultured in 400 ml of LB liquid (containing 50 µg/ml ampicillin) at 30° C. for 16 hours. Centrifugation gave the cells. After 20 ml of a solution given by Table 12 containing the obtained cells and a strain having ATP regenerating activity (Japanese Published Unexamined Patent Application No. 74595/86) was incubated at 30° C. for 20 hours at pH of 7.6, an amount of 5'-IMP produced in the solution was quantitatively assayed and found to be 25 g/l (calculated as the hydrate). Also in the case of using a strain carrying a recombinant DNA containing a DNA molecule, in which part of the structural gene, i.e., the sequence subsequent to the 8th Leu from the C terminal has modified to have the following amino acid sequence: GlyMetGlnAlaGlyThrGluLeuGluPheThrGlyArg-ArgPheThrThrSer, a similar titer can be obtained.

TABLE 12

| Composition of reaction solution | |
| --- | --- |
| Cells of *Brevibacterium ammoniagenes* ATCC21477 (ATP-regenerating cell) | 200 g wet cell weight/l |
| Inosine-guanosine kinase amplified *Escherichia coli* | 25 g wet cell weight/l |
| Inosine | 12.5 g/l |
| Monopotassium phosphate | 20 g/l |
| Glucose | 50 g/l |
| Magnesium sulfate | 5 g/l |
| Xylene | 10 ml/l |

INDUSTRIAL APPLICABILITY

According to the present invention, inosine-guanosine kinase derived from a microorganism belonging to the genus *Escherichia* can be provided. In addition, clarification of various properties of the enzyme for the first time has led to industrial utilization thereof. Furthermore, DNA encoding the enzyme has been isolated. Using as a catalyst a microorganism containing the recombinant DNA obtained by introducing this DNA into a vector, 5'-nucleotides, e.g., 5'-IMP or 5'-GMP, can be produced from nucleosides, e.g., inosine or guanosine, in a high conversion rate.

SEQUENCE LISTING ( 1 ) GENERAL INFORMATION:

( i i i ) NUMBER OF SEQUENCES: 4

( 2 ) INFORMATION FOR SEQ ID NO:1:

( i ) SEQUENCE CHARACTERISTICS:
        ( A ) LENGTH: 1302 base pairs
        ( B ) TYPE: nucleic acid
        ( C ) STRANDEDNESS: double
        ( D ) TOPOLOGY: linear ( i i ) MOLECULE TYPE: DNA (genomic)

( i i i ) HYPOTHETICAL: NO ( i v ) ANTI-SENSE: NO ( v i ) ORIGINAL SOURCE:
        ( A ) ORGANISM: Escherichia coli
        ( B ) STRAIN: K12
        ( C ) INDIVIDUAL ISOLATE: HM70

( v i i ) IMMEDIATE SOURCE:
        ( B ) CLONE: pBM1

( i x ) FEATURE:
        ( A ) NAME/KEY: CDS
        ( B ) LOCATION: 1..1302

( x i ) SEQUENCE DESCRIPTION: SEQ ID NO:1:

```
ATG AAA TTT CCC GGT AAA CGT AAA TCC AAA CAT TAC TTC CCC GTA AAC         48
Met Lys Phe Pro Gly Lys Arg Lys Ser Lys His Tyr Phe Pro Val Asn
 1               5                  10                  15

GCA CGC GAT CCG CTG CTT CAG CAA TTC CAG CCA GAA AAC GAA ACC AGC         96
Ala Arg Asp Pro Leu Leu Gln Gln Phe Gln Pro Glu Asn Glu Thr Ser
             20                  25                  30

GCT GCC TGG GTA GTG GGT ATC GAT CAA ACG CTG GTC GAT ATT GAA GCG        144
Ala Ala Trp Val Val Gly Ile Asp Gln Thr Leu Val Asp Ile Glu Ala
         35                  40                  45

AAA GTG GAT GAT GAA TTT ATT GAG CGT TAT GGA TTA AGC GCC GGG CAT        192
Lys Val Asp Asp Glu Phe Ile Glu Arg Tyr Gly Leu Ser Ala Gly His
     50                  55                  60

TCA CTG GTG ATT GAG GAT GAT GTA GCC GAA GCG CTT TAT CAG GAA CTA        240
Ser Leu Val Ile Glu Asp Asp Val Ala Glu Ala Leu Tyr Gln Glu Leu
 65                  70                  75                  80

AAA CAG AAA AAC CTG ATT ACC CAT CAG TTT GCG GGT GGC ACC ATT GGT        288
Lys Gln Lys Asn Leu Ile Thr His Gln Phe Ala Gly Gly Thr Ile Gly
                 85                  90                  95

AAC ACC ATG CAC AAC TAC TCG GTG CTC GCG GAC GAC CGT TCG GTG CTG        336
Asn Thr Met His Asn Tyr Ser Val Leu Ala Asp Asp Arg Ser Val Leu
            100                 105                 110

CTG GGC GTC ATG TGC AGC AAT ATT GAA ATT GGC AGT TAT GCC TAT CGT        384
Leu Gly Val Met Cys Ser Asn Ile Glu Ile Gly Ser Tyr Ala Tyr Arg
        115                 120                 125

TAC CTG TGT AAC ACT TCC AGC CGT ACC GAT CTT AAC TAT CTA CAA GGC        432
Tyr Leu Cys Asn Thr Ser Ser Arg Thr Asp Leu Asn Tyr Leu Gln Gly
    130                 135                 140

GTG GAT GGC CCG ATT GGT CGT TGC TTT ACG CTG ATT GGC GAG TCC GGG        480
Val Asp Gly Pro Ile Gly Arg Cys Phe Thr Leu Ile Gly Glu Ser Gly
145                 150                 155                 160

GAA CGT ACC TTT GCT ATC AGT CCA GGC CAC ATG AAC CAG CTG CGG GCT        528
Glu Arg Thr Phe Ala Ile Ser Pro Gly His Met Asn Gln Leu Arg Ala
                165                 170                 175
```

```
GAA  AGC  ATT  CCG  GAA  GAT  GTG  ATT  GCC  GGA  GCC  TCG  GCA  CTG  GTT  CTC     576
Glu  Ser  Ile  Pro  Glu  Asp  Val  Ile  Ala  Gly  Ala  Ser  Ala  Leu  Val  Leu
          180                      185                     190

ACC  TCA  TAT  CTG  GTG  CGT  TGC  AAG  CCG  GGT  GAA  CCC  ATG  CCG  GAA  GCA     624
Thr  Ser  Tyr  Leu  Val  Arg  Cys  Lys  Pro  Gly  Glu  Pro  Met  Pro  Glu  Ala
          195                      200                     205

ACC  ATG  AAA  GCC  ATT  GAG  TAC  GCG  AAG  AAA  TAT  AAC  GTA  CCG  GTG  GTG     672
Thr  Met  Lys  Ala  Ile  Glu  Tyr  Ala  Lys  Lys  Tyr  Asn  Val  Pro  Val  Val
     210                      215                     220

CTG  ACG  CTG  GGC  ACC  AAG  TTT  GTC  ATT  GCC  GAG  AAT  CCG  CAG  TGG  TGG     720
Leu  Thr  Leu  Gly  Thr  Lys  Phe  Val  Ile  Ala  Glu  Asn  Pro  Gln  Trp  Trp
225                     230                      235                     240

CAG  CAA  TTC  CTC  AAA  GAT  CAC  GTC  TCT  ATC  CTT  GCG  ATG  AAC  GAA  GAT     768
Gln  Gln  Phe  Leu  Lys  Asp  His  Val  Ser  Ile  Leu  Ala  Met  Asn  Glu  Asp
               245                      250                     255

GAA  GCC  GAA  GCG  TTG  ACC  GGA  GAA  AGC  GAT  CCG  TTG  TTG  GCA  TCT  GAC     816
Glu  Ala  Glu  Ala  Leu  Thr  Gly  Glu  Ser  Asp  Pro  Leu  Leu  Ala  Ser  Asp
                260                      265                     270

AAG  GCG  CTG  GAC  TGG  GTA  GAT  CTG  GTG  CTG  TGC  ACC  GCC  GGG  CCA  ATC     864
Lys  Ala  Leu  Asp  Trp  Val  Asp  Leu  Val  Leu  Cys  Thr  Ala  Gly  Pro  Ile
          275                      280                     285

GGC  TTG  TAT  ATG  GCG  GGC  TTT  ACC  GAA  GAC  GAA  GCG  AAA  CGT  AAA  ACC     912
Gly  Leu  Tyr  Met  Ala  Gly  Phe  Thr  Glu  Asp  Glu  Ala  Lys  Arg  Lys  Thr
290                     295                      300

CAG  CAT  CCG  CTG  CTG  CCG  GGC  GCT  ATA  GCG  GAA  TTC  AAC  CAG  TAT  GAG     960
Gln  His  Pro  Leu  Leu  Pro  Gly  Ala  Ile  Ala  Glu  Phe  Asn  Gln  Tyr  Glu
305                     310                      315                     320

TTT  AGC  CGC  GCC  ATG  CGC  CAC  AAG  GAT  TGC  CAG  AAT  CCG  CTG  CGT  GTA    1008
Phe  Ser  Arg  Ala  Met  Arg  His  Lys  Asp  Cys  Gln  Asn  Pro  Leu  Arg  Val
               325                      330                     335

TAT  TCG  CAC  ATT  GCG  CCG  TAC  ATG  GGC  GGG  CCG  GAA  AAA  ATC  ATG  AAC    1056
Tyr  Ser  His  Ile  Ala  Pro  Tyr  Met  Gly  Gly  Pro  Glu  Lys  Ile  Met  Asn
                340                      345                     350

ACT  AAT  GGA  GCG  GGG  GAT  GGC  GCA  TTG  GCA  GCG  TTG  CTG  CAT  GAC  ATT    1104
Thr  Asn  Gly  Ala  Gly  Asp  Gly  Ala  Leu  Ala  Ala  Leu  Leu  His  Asp  Ile
          355                      360                     365

ACC  GCC  AAC  AGC  TAC  CAT  CGT  AGC  AAC  GTA  CCA  AAC  TCC  AGC  AAA  CAT    1152
Thr  Ala  Asn  Ser  Tyr  His  Arg  Ser  Asn  Val  Pro  Asn  Ser  Ser  Lys  His
370                     375                      380

AAA  TTC  ACC  TGG  TTA  ACT  TAT  TCA  TCG  TTA  GCG  CAG  GTG  TGT  AAA  TAT    1200
Lys  Phe  Thr  Trp  Leu  Thr  Tyr  Ser  Ser  Leu  Ala  Gln  Val  Cys  Lys  Tyr
385                     390                      395                     400

GCT  AAC  CGT  GTG  AGC  TAT  CAG  GTA  CTG  AAC  CAG  CAT  TCA  CCT  CGT  TTA    1248
Ala  Asn  Arg  Val  Ser  Tyr  Gln  Val  Leu  Asn  Gln  His  Ser  Pro  Arg  Leu
               405                      410                     415

ACG  CGC  GGC  TTG  CCG  GAG  CGT  GAA  GAC  AGC  CTG  GAA  GAG  TCT  TAC  TGG    1296
Thr  Arg  Gly  Leu  Pro  Glu  Arg  Glu  Asp  Ser  Leu  Glu  Glu  Ser  Tyr  Trp
                420                      425                     430

GAT  CGT                                                                          1302
Asp  Arg
```

( 2 ) INFORMATION FOR SEQ ID NO:2:

( i ) SEQUENCE CHARACTERISTICS:
        ( A ) LENGTH: 434 amino acids
        ( B ) TYPE: amino acid
        ( D ) TOPOLOGY: linear ( i i ) MOLECULE TYPE: protein ( x i ) SEQUENCE DESCRIPTION: SEQ ID NO:2:

Met  Lys  Phe  Pro  Gly  Lys  Arg  Lys  Ser  Lys  His  Tyr  Phe  Pro  Val  Asn

|   1   |       |       |       |   5   |       |       |       |       |  10   |       |       |       |       |  15   |
|-------|-------|-------|-------|-------|-------|-------|-------|-------|-------|-------|-------|-------|-------|-------|
| Ala   | Arg   | Asp   | Pro   | Leu   | Leu   | Gln   | Gln   | Phe   | Gln   | Pro   | Glu   | Asn   | Glu   | Thr   | Ser |

Ala Arg Asp Pro Leu Leu Gln Gln Phe Gln Pro Glu Asn Glu Thr Ser
                20                      25                30

Ala Ala Trp Val Val Gly Ile Asp Gln Thr Leu Val Asp Ile Glu Ala
            35              40                      45

Lys Val Asp Asp Glu Phe Ile Glu Arg Tyr Gly Leu Ser Ala Gly His
        50              55                  60

Ser Leu Val Ile Glu Asp Val Ala Glu Ala Leu Tyr Gln Glu Leu
65              70                  75                      80

Lys Gln Lys Asn Leu Ile Thr His Gln Phe Ala Gly Gly Thr Ile Gly
                85                  90                      95

Asn Thr Met His Asn Tyr Ser Val Leu Ala Asp Asp Arg Ser Val Leu
            100             105                 110

Leu Gly Val Met Cys Ser Asn Ile Glu Ile Gly Ser Tyr Ala Tyr Arg
        115                 120                 125

Tyr Leu Cys Asn Thr Ser Ser Arg Thr Asp Leu Asn Tyr Leu Gln Gly
    130                 135                 140

Val Asp Gly Pro Ile Gly Arg Cys Phe Thr Leu Ile Gly Glu Ser Gly
145             150                 155                     160

Glu Arg Thr Phe Ala Ile Ser Pro Gly His Met Asn Gln Leu Arg Ala
            165                 170                 175

Glu Ser Ile Pro Glu Asp Val Ile Ala Gly Ala Ser Ala Leu Val Leu
        180                 185                 190

Thr Ser Tyr Leu Val Arg Cys Lys Pro Gly Glu Pro Met Pro Glu Ala
    195                 200                 205

Thr Met Lys Ala Ile Glu Tyr Ala Lys Lys Tyr Asn Val Pro Val Val
    210                 215                 220

Leu Thr Leu Gly Thr Lys Phe Val Ile Ala Glu Asn Pro Gln Trp Trp
225                 230                 235                 240

Gln Gln Phe Leu Lys Asp His Val Ser Ile Leu Ala Met Asn Glu Asp
            245                 250                 255

Glu Ala Glu Ala Leu Thr Gly Glu Ser Asp Pro Leu Leu Ala Ser Asp
            260                 265                 270

Lys Ala Leu Asp Trp Val Asp Leu Val Leu Cys Thr Ala Gly Pro Ile
        275                 280                 285

Gly Leu Tyr Met Ala Gly Phe Thr Glu Asp Glu Ala Lys Arg Lys Thr
    290                 295                 300

Gln His Pro Leu Leu Pro Gly Ala Ile Ala Glu Phe Asn Gln Tyr Glu
305                 310                 315                 320

Phe Ser Arg Ala Met Arg His Lys Asp Cys Gln Asn Pro Leu Arg Val
                325                 330                 335

Tyr Ser His Ile Ala Pro Tyr Met Gly Gly Pro Glu Lys Ile Met Asn
            340                 345                 350

Thr Asn Gly Ala Gly Asp Gly Ala Leu Ala Ala Leu Leu His Asp Ile
        355                 360                 365

Thr Ala Asn Ser Tyr His Arg Ser Asn Val Pro Asn Ser Ser Lys His
    370                 375                 380

Lys Phe Thr Trp Leu Thr Tyr Ser Ser Leu Ala Gln Val Cys Lys Tyr
385                 390                 395                 400

Ala Asn Arg Val Ser Tyr Gln Val Leu Asn Gln His Ser Pro Arg Leu
                405                 410                 415

Thr Arg Gly Leu Pro Glu Arg Glu Asp Ser Leu Glu Glu Ser Tyr Trp
            420                 425                 430

Asp Arg (2) INFORMATION FOR SEQ ID NO:3:

(i) SEQUENCE CHARACTERISTICS:
        (A) LENGTH: 1335 base pairs
        (B) TYPE: nucleic acid
        (C) STRANDEDNESS: double
        (D) TOPOLOGY: linear (ii) MOLECULE TYPE: DNA (genomic)

(iii) HYPOTHETICAL: NO (iv) ANTI-SENSE: NO (vi) ORIGINAL SOURCE:
        (A) ORGANISM: Escherichia coli
        (B) STRAIN: K12
        (C) INDIVIDUAL ISOLATE: HM70

(ix) FEATURE:
        (A) NAME/KEY: CDS
        (B) LOCATION: complement (1..1335)

(ix) FEATURE:
        (A) NAME/KEY: CDS
        (B) LOCATION: 1..1335

(xi) SEQUENCE DESCRIPTION: SEQ ID NO:3:

```
ATG AAA TTT CCC GGT AAA CGT AAA TCC AAA CAT TAC TTC CCC GTA AAC      48
Met Lys Phe Pro Gly Lys Arg Lys Ser Lys His Tyr Phe Pro Val Asn
 1               5                  10                  15

GCA CGC GAT CCG CTG CTT CAG CAA TTC CAG CCA GAA AAC GAA ACC AGC      96
Ala Arg Asp Pro Leu Leu Gln Gln Phe Gln Pro Glu Asn Glu Thr Ser
             20                  25                  30

GCT GCC TGG GTA GTG GGT ATC GAT CAA ACG CTG GTC GAT ATT GAA GCG     144
Ala Ala Trp Val Val Gly Ile Asp Gln Thr Leu Val Asp Ile Glu Ala
         35                  40                  45

AAA GTG GAT GAT GAA TTT ATT GAG CGT TAT GGA TTA AGC GCC GGG CAT     192
Lys Val Asp Asp Glu Phe Ile Glu Arg Tyr Gly Leu Ser Ala Gly His
     50                  55                  60

TCA CTG GTG ATT GAG GAT GAT GTA GCC GAA GCG CTT TAT CAG GAA CTA     240
Ser Leu Val Ile Glu Asp Asp Val Ala Glu Ala Leu Tyr Gln Glu Leu
 65                  70                  75                  80

AAA CAG AAA AAC CTG ATT ACC CAT CAG TTT GCG GGT GGC ACC ATT GGT     288
Lys Gln Lys Asn Leu Ile Thr His Gln Phe Ala Gly Gly Thr Ile Gly
                 85                  90                  95

AAC ACC ATG CAC AAC TAC TCG GTG CTC GCG GAC GAC CGT TCG GTG CTG     336
Asn Thr Met His Asn Tyr Ser Val Leu Ala Asp Asp Arg Ser Val Leu
            100                 105                 110

CTG GGC GTC ATG TGC AGC AAT ATT GAA ATT GGC AGT TAT GCC TAT CGT     384
Leu Gly Val Met Cys Ser Asn Ile Glu Ile Gly Ser Tyr Ala Tyr Arg
        115                 120                 125

TAC CTG TGT AAC ACT TCC AGC CGT ACC GAT CTT AAC TAT CTA CAA GGC     432
Tyr Leu Cys Asn Thr Ser Ser Arg Thr Asp Leu Asn Tyr Leu Gln Gly
    130                 135                 140

GTG GAT GGC CCG ATT GGT CGT TGC TTT ACG CTG ATT GGC GAG TCC GGG     480
Val Asp Gly Pro Ile Gly Arg Cys Phe Thr Leu Ile Gly Glu Ser Gly
145                 150                 155                 160

GAA CGT ACC TTT GCT ATC AGT CCA GGC CAC ATG AAC CAG CTG CGG GCT     528
Glu Arg Thr Phe Ala Ile Ser Pro Gly His Met Asn Gln Leu Arg Ala
                165                 170                 175

GAA AGC ATT CCG GAA GAT GTG ATT GCC GGA GCC TCG GCA CTG GTT CTC     576
Glu Ser Ile Pro Glu Asp Val Ile Ala Gly Ala Ser Ala Leu Val Leu
            180                 185                 190
```

| | | | | | | | | | | | | | | | | |
|---|---|---|---|---|---|---|---|---|---|---|---|---|---|---|---|---|
| ACC | TCA | TAT | CTG | GTG | CGT | TGC | AAG | CCG | GGT | GAA | CCC | ATG | CCG | GAA | GCA | 624 |
| Thr | Ser | Tyr | Leu | Val | Arg | Cys | Lys | Pro | Gly | Glu | Pro | Met | Pro | Glu | Ala | |
| | 195 | | | | | | 200 | | | | | 205 | | | | |
| ACC | ATG | AAA | GCC | ATT | GAG | TAC | GCG | AAG | AAA | TAT | AAC | GTA | CCG | GTG | GTG | 672 |
| Thr | Met | Lys | Ala | Ile | Glu | Tyr | Ala | Lys | Lys | Tyr | Asn | Val | Pro | Val | Val | |
| | 210 | | | | 215 | | | | | 220 | | | | | | |
| CTG | ACG | CTG | GGC | ACC | AAG | TTT | GTC | ATT | GCC | GAG | AAT | CCG | CAG | TGG | TGG | 720 |
| Leu | Thr | Leu | Gly | Thr | Lys | Phe | Val | Ile | Ala | Glu | Asn | Pro | Gln | Trp | Trp | |
| 225 | | | | | 230 | | | | | 235 | | | | | 240 | |
| CAG | CAA | TTC | CTC | AAA | GAT | CAC | GTC | TCT | ATC | CTT | GCG | ATG | AAC | GAA | GAT | 768 |
| Gln | Gln | Phe | Leu | Lys | Asp | His | Val | Ser | Ile | Leu | Ala | Met | Asn | Glu | Asp | |
| | | | | 245 | | | | | 250 | | | | | 255 | | |
| GAA | GCC | GAA | GCG | TTG | ACC | GGA | GAA | AGC | GAT | CCG | TTG | TTG | GCA | TCT | GAC | 816 |
| Glu | Ala | Glu | Ala | Leu | Thr | Gly | Glu | Ser | Asp | Pro | Leu | Leu | Ala | Ser | Asp | |
| | | | | 260 | | | | | 265 | | | | 270 | | | |
| AAG | GCG | CTG | GAC | TGG | GTA | GAT | CTG | GTG | CTG | TGC | ACC | GCC | GGG | CCA | ATC | 864 |
| Lys | Ala | Leu | Asp | Trp | Val | Asp | Leu | Val | Leu | Cys | Thr | Ala | Gly | Pro | Ile | |
| | | | 275 | | | | | 280 | | | | | 285 | | | |
| GGC | TTG | TAT | ATG | GCG | GGC | TTT | ACC | GAA | GAC | GAA | GCG | AAA | CGT | AAA | ACC | 912 |
| Gly | Leu | Tyr | Met | Ala | Gly | Phe | Thr | Glu | Asp | Glu | Ala | Lys | Arg | Lys | Thr | |
| | | 290 | | | | | 295 | | | | | 300 | | | | |
| CAG | CAT | CCG | CTG | CTG | CCG | GGC | GCT | ATA | GCG | GAA | TTC | AAC | CAG | TAT | GAG | 960 |
| Gln | His | Pro | Leu | Leu | Pro | Gly | Ala | Ile | Ala | Glu | Phe | Asn | Gln | Tyr | Glu | |
| 305 | | | | | 310 | | | | | 315 | | | | | 320 | |
| TTT | AGC | CGC | GCC | ATG | CGC | CAC | AAG | GAT | TGC | CAG | AAT | CCG | CTG | CGT | GTA | 1008 |
| Phe | Ser | Arg | Ala | Met | Arg | His | Lys | Asp | Cys | Gln | Asn | Pro | Leu | Arg | Val | |
| | | | | 325 | | | | | 330 | | | | | 335 | | |
| TAT | TCG | CAC | ATT | GCG | CCG | TAC | ATG | GGC | GGG | CCG | GAA | AAA | ATC | ATG | AAC | 1056 |
| Tyr | Ser | His | Ile | Ala | Pro | Tyr | Met | Gly | Gly | Pro | Glu | Lys | Ile | Met | Asn | |
| | | | 340 | | | | | 345 | | | | | 350 | | | |
| ACT | AAT | GGA | GCG | GGG | GAT | GGC | GCA | TTG | GCA | GCG | TTG | CTG | CAT | GAC | ATT | 1104 |
| Thr | Asn | Gly | Ala | Gly | Asp | Gly | Ala | Leu | Ala | Ala | Leu | Leu | His | Asp | Ile | |
| | | 355 | | | | | 360 | | | | | 365 | | | | |
| ACC | GCC | AAC | AGC | TAC | CAT | CGT | AGC | AAC | GTA | CCA | AAC | TCC | AGC | AAA | CAT | 1152 |
| Thr | Ala | Asn | Ser | Tyr | His | Arg | Ser | Asn | Val | Pro | Asn | Ser | Ser | Lys | His | |
| | 370 | | | | | 375 | | | | | 380 | | | | | |
| AAA | TTC | ACC | TGG | TTA | ACT | TAT | TCA | TCG | TTA | GCG | CAG | GTG | TGT | AAA | TAT | 1200 |
| Lys | Phe | Thr | Trp | Leu | Thr | Tyr | Ser | Ser | Leu | Ala | Gln | Val | Cys | Lys | Tyr | |
| 385 | | | | | 390 | | | | | 395 | | | | | 400 | |
| GCT | AAC | CGT | GTG | AGC | TAT | CAG | GTA | CTG | AAC | CAG | CAT | TCA | CCT | CGT | TTA | 1248 |
| Ala | Asn | Arg | Val | Ser | Tyr | Gln | Val | Leu | Asn | Gln | His | Ser | Pro | Arg | Leu | |
| | | | | 405 | | | | | 410 | | | | | 415 | | |
| ACG | CGC | GGC | TTG | CCG | GAG | CGT | GAA | GAC | AGC | CTG | GGC | ATG | CAA | GCG | GGT | 1296 |
| Thr | Arg | Gly | Leu | Pro | Glu | Arg | Glu | Asp | Ser | Leu | Gly | Met | Gln | Ala | Gly | |
| | | | 420 | | | | | 425 | | | | | 430 | | | |
| ACC | GAG | CTC | GAA | TTC | ACT | GGC | CGT | CGT | TTT | ACA | ACG | TCG | | | | 1335 |
| Thr | Glu | Leu | Glu | Phe | Thr | Gly | Arg | Arg | Phe | Thr | Thr | Ser | | | | |
| | | 435 | | | | | 440 | | | | | 445 | | | | |

( 2 ) INFORMATION FOR SEQ ID NO:4:

( i ) SEQUENCE CHARACTERISTICS:
        ( A ) LENGTH: 445 amino acids
        ( B ) TYPE: amino acid
        ( D ) TOPOLOGY: linear ( i i ) MOLECULE TYPE: protein ( x i ) SEQUENCE DESCRIPTION: SEQ ID NO:4:

| | | | | | | | | | | | | | | | |
|---|---|---|---|---|---|---|---|---|---|---|---|---|---|---|---|
| Met | Lys | Phe | Pro | Gly | Lys | Arg | Lys | Ser | Lys | His | Tyr | Phe | Pro | Val | Asn |
| 1 | | | | 5 | | | | | 10 | | | | | 15 | |
| Ala | Arg | Asp | Pro | Leu | Leu | Gln | Gln | Phe | Gln | Pro | Glu | Asn | Glu | Thr | Ser |

|     |     |     |     |     | 20  |     |     |     |     |     |     | 25  |     |     |     |     |     | 30  |     |     |
| --- | --- | --- | --- | --- | --- | --- | --- | --- | --- | --- | --- | --- | --- | --- | --- | --- | --- | --- | --- | --- |
| Ala | Ala | Trp<br>35 | Val | Val | Gly | Ile | Asp<br>40 | Gln | Thr | Leu | Val | Asp<br>45 | Ile | Glu | Ala |
| Lys | Val<br>50 | Asp | Asp | Glu | Phe | Ile<br>55 | Glu | Arg | Tyr | Gly | Leu<br>60 | Ser | Ala | Gly | His |
| Ser<br>65 | Leu | Val | Ile | Glu | Asp<br>70 | Asp | Val | Ala | Glu | Ala<br>75 | Leu | Tyr | Gln | Glu | Leu<br>80 |
| Lys | Gln | Lys | Asn | Leu<br>85 | Ile | Thr | His | Gln | Phe<br>90 | Ala | Gly | Gly | Thr | Ile<br>95 | Gly |
| Asn | Thr | Met | His<br>100 | Asn | Tyr | Ser | Val | Leu<br>105 | Ala | Asp | Asp | Arg | Ser<br>110 | Val | Leu |
| Leu | Gly | Val<br>115 | Met | Cys | Ser | Asn | Ile<br>120 | Glu | Ile | Gly | Ser | Tyr<br>125 | Ala | Tyr | Arg |
| Tyr | Leu<br>130 | Cys | Asn | Thr | Ser | Ser<br>135 | Arg | Thr | Asp | Leu | Asn<br>140 | Tyr | Leu | Gln | Gly |
| Val<br>145 | Asp | Gly | Pro | Ile | Gly<br>150 | Arg | Cys | Phe | Thr | Leu<br>155 | Ile | Gly | Glu | Ser | Gly<br>160 |
| Glu | Arg | Thr | Phe | Ala<br>165 | Ile | Ser | Pro | Gly | His<br>170 | Met | Asn | Gln | Leu | Arg<br>175 | Ala |
| Glu | Ser | Ile | Pro<br>180 | Glu | Asp | Val | Ile | Ala<br>185 | Gly | Ala | Ser | Ala | Leu<br>190 | Val | Leu |
| Thr | Ser | Tyr<br>195 | Leu | Val | Arg | Cys | Lys<br>200 | Pro | Gly | Glu | Pro | Met<br>205 | Pro | Glu | Ala |
| Thr | Met<br>210 | Lys | Ala | Ile | Glu | Tyr<br>215 | Ala | Lys | Lys | Tyr | Asn<br>220 | Val | Pro | Val | Val |
| Leu<br>225 | Thr | Leu | Gly | Thr | Lys<br>230 | Phe | Val | Ile | Ala | Glu<br>235 | Asn | Pro | Gln | Trp | Trp<br>240 |
| Gln | Gln | Phe | Leu | Lys<br>245 | Asp | His | Val | Ser | Ile<br>250 | Leu | Ala | Met | Asn | Glu<br>255 | Asp |
| Glu | Ala | Glu | Ala<br>260 | Leu | Thr | Gly | Glu | Ser<br>265 | Asp | Pro | Leu | Leu | Ala<br>270 | Ser | Asp |
| Lys | Ala | Leu<br>275 | Asp | Trp | Val | Asp | Leu<br>280 | Val | Leu | Cys | Thr | Ala<br>285 | Gly | Pro | Ile |
| Gly | Leu<br>290 | Tyr | Met | Ala | Gly | Phe<br>295 | Thr | Glu | Asp | Glu | Ala<br>300 | Lys | Arg | Lys | Thr |
| Gln<br>305 | His | Pro | Leu | Leu | Pro<br>310 | Gly | Ala | Ile | Ala | Glu<br>315 | Phe | Asn | Gln | Tyr | Glu<br>320 |
| Phe | Ser | Arg | Ala | Met<br>325 | Arg | His | Lys | Asp | Cys<br>330 | Gln | Asn | Pro | Leu | Arg<br>335 | Val |
| Tyr | Ser | His | Ile<br>340 | Ala | Pro | Tyr | Met | Gly<br>345 | Gly | Pro | Glu | Lys | Ile<br>350 | Met | Asn |
| Thr | Asn | Gly<br>355 | Ala | Gly | Asp | Gly | Ala<br>360 | Leu | Ala | Ala | Leu | Leu<br>365 | His | Asp | Ile |
| Thr | Ala<br>370 | Asn | Ser | Tyr | His | Arg<br>375 | Ser | Asn | Val | Pro | Asn<br>380 | Ser | Ser | Lys | His |
| Lys<br>385 | Phe | Thr | Trp | Leu | Thr<br>390 | Tyr | Ser | Ser | Leu | Ala<br>395 | Gln | Val | Cys | Lys | Tyr<br>400 |
| Ala | Asn | Arg | Val | Ser<br>405 | Tyr | Gln | Val | Leu | Asn<br>410 | Gln | His | Ser | Pro | Arg<br>415 | Leu |
| Thr | Arg | Gly | Leu<br>420 | Pro | Glu | Arg | Glu | Asp<br>425 | Ser | Leu | Gly | Met | Gln<br>430 | Ala | Gly |
| Thr | Glu | Leu<br>435 | Glu | Phe | Thr | Gly | Arg<br>440 | Arg | Phe | Thr | Thr | Ser<br>445 |

We claim:

1. An isolated and purified gene that encodes an inosine-guanosine kinase having the amino acid sequence shown by SEQ ID NO. 2.

2. The gene as claimed in claim 1, wherein said gene comprises the nucleotide sequence SEQ ID NO. 1.

3. The gene as claimed in claims 1 or 2, wherein said gene is derived from *Escherichia coli*.

4. A recombinant DNA molecule comprising a vector containing the gene according to claims 1 or 2.

5. A microorganism containing a recombinant DNA molecule comprising a vector containing the gene according to claims 1 or 2.

6. The microorganism as claimed in claim 5, wherein said microorganism is *Escherichia coli*.

7. A process for preparing an inosine-guanosine kinase which comprises the steps of:
   (i) culturing in a medium a microorganism carrying a recombinant DNA molecule comprising a vector containing the gene according to claims 1 or 2;
   (ii) producing and accumulating the inosine-guanosine kinase in the cultured cells; and
   (iii) collecting the inosine-guanosine kinase from the cultured cells.

8. A microorganism containing a recombinant DNA molecule comprising a vector containing the gene according to claims 1 or 2, wherein said gene is derived from *Escherichia coli*.

9. A process for preparing 5'-IMP or 5'-GMP which comprises the steps of:

(i) reacting inosine or guanosine with a phosphate donor comprising UTP, ATP or dATP in an aqueous medium in the presence of a cell or culture broth of a microorganism transformed with a gene according to claims 1 or 2;

(ii) producing an accumulating 5'-IMP or 5'-GMP in the reaction mixture; and (iii) collecting 5'-IMP or 5'-GMP from the reaction mixture.

10. The process claimed in claim 9, wherein said phosphate donor is ATP or DATP.

11. The process as claimed in claim 9, wherein said microorganism is a microorganism containing a recombinant DNA molecule comprising a vector containing the gene that has sequence SEQ ID NO. 1.

12. A process for preparing an inosine-guanosine kinase which comprises the steps of:
   (i) culturing in a medium a microorganism carrying a recombinant DNA molecule comprising a vector containing the gene according to claims 1 or 2, wherein said gene is derived from *Escherichia coli*;
   (ii) producing and accumulating the inosine-guanosine kinase in the cultured cells; and
   (iii) collecting the inosine-guanosine kinase from the cultured cells.

* * * * *

UNITED STATES PATENT AND TRADEMARK OFFICE
CERTIFICATE OF CORRECTION

PATENT NO. : 5,756,315

DATED : May 26, 1998

INVENTOR(S): HIDEO MORI ET AL.

Page 1 of 6

It is certified that error appears in the above-identified patent and that said Letters Patent is hereby corrected as shown below:

ON COVER PAGE AT [56], OTHER PUBLICATIONS

"No new references are cited. Please see PTOL 892 attached to paper 11." should be deleted.

"Maniatis et al. ... etc.", "Combes et al. ... etc." and "Le Page et al. ... etc." (2nd occurrence) should be deleted.

ON COVER PAGE AT [57]

"12 Claims" should read --14 Claims--.

SHEET 7

"INDSINE-GUANDSINE" should read --INOSINE-GUANOSINE--.

COLUMN 1

Line 33, "fermentation" should read --fermentation.--;

COLUMN 2

Line 31, "the" should read --to the--;
Line 41, "variety" should read --with a variety--.

UNITED STATES PATENT AND TRADEMARK OFFICE
CERTIFICATE OF CORRECTION

PATENT NO. : 5,756,315

DATED : May 26, 1998

INVENTOR(S): HIDEO MORI ET AL.

It is certified that error appears in the above-identified patent and that said Letters Patent is hereby corrected as shown below:

COLUMN 3

Line 15, "rium" should read --rium,--;
Line 16, "EM70" should read --HM70--;
Line 59, "inosine guanosine" should read
 --inosine-guanosine--.

COLUMN 4

Line 7, "form:" should read --forming--;
Line 52, "convent" should read --conventional--.

COLUMN 11

Line 19, "interfere" should read --interfere with--.

COLUMN 14

Line 46, "Ltd.)" should read --Ltd.).--;

COLUMN 15

Line 18, "conc. HCl." should read --conc. HCl--.

UNITED STATES PATENT AND TRADEMARK OFFICE
CERTIFICATE OF CORRECTION

PATENT NO. : 5,756,315

DATED : May 26, 1998

INVENTOR(S): HIDEO MORI ET AL.

It is certified that error appears in the above-identified patent and that said Letters Patent is hereby corrected as shown below:

COLUMN 16

Table 7, line 12, "acicd" should read --acid--;
Line 55, "5'-nucleotides" should read --5'-Nucleotides--.

COLUMN 17

Line 26, "obained" should read --obtained--.

COLUMN 18

Line 38, "inosine guanosine-" should read
  --inosine-guanosine--.

COLUMN 20

Line 29, "has" should read --has been--.

COLUMN 21

"SEQUENCE LISTING
(I) GENERAL INFORMATION:

(iii) NUMBER OF SEQUENCES: 4" should read

UNITED STATES PATENT AND TRADEMARK OFFICE
CERTIFICATE OF CORRECTION

PATENT NO. : 5,756,315

DATED : May 26, 1998

INVENTOR(S): HIDEO MORI ET AL.

It is certified that error appears in the above-identified patent and that said Letters Patent is hereby corrected as shown below:

COLUMN 21

--SEQUENCE LISTING
(I) GENERAL INFORMATION:

(i)   APPLICANT:   Hideo, Mori
                              Akihiro, Iida
                              Sadao, Teshiba
                              Tatsuro, Fujio (ii)   TITLE OF INVENTION: INOSINE-GUANOSINE KINASE (iii)   NUMBER OF SEQUENCES: 4

(iv)   CORRESPONDENCE ADDRESS:
           (A)   ADDRESSEE: FITZPATRICK, CELLA, HARPER & SCINTO
           (B)   STREET: 277 Park Avenue
           (C)   CITY: New York
           (D)   STATE: N.Y.
           (E)   COUNTRY: U.S.A.
           (F)   ZIP: 10172

(v)   COMPUTER READABLE FORM:
           (A)   MEDIUM TYPE: Floppy disk
           (B)   COMPUTER: IBM PC compatible
           (C)   OPERATING SYSTEM: PC-DOS/MS-DOS
           (D)   SOFTWARE: PatentIn Release #1.0, Version #1.25

UNITED STATES PATENT AND TRADEMARK OFFICE
CERTIFICATE OF CORRECTION

PATENT NO. : 5,756,315

DATED : May 26, 1998

INVENTOR(S): HIDEO MORI ET AL.

It is certified that error appears in the above-identified patent and that said Letters Patent is hereby corrected as shown below:

<u>COLUMN 21</u>

```
   (vi)     CURRENT APPLICATION DATA:
            (A)  APPLICATION NUMBER:
            (B)  FILING DATE:
            (C)  CLASSIFICATION:

(vii)    PRIOR APPLICATION DATA:
            (A)  APPLICATION NUMBER: JP 89/315537
            (B)  FILING DATE:  05-DEC-1989

(viii)   ATTORNEY/AGENT INFORMATION
            (A)  NAME:  Perry, Lawrence S.
            (B)  REGISTRATION NUMBER:  31865

(ix)     TELECOMMUNICATION INFORMATION
            (A)  TELEPHONE: 212-218-2100
            (B)  TELEFAX: 212-218-2200        --
```

UNITED STATES PATENT AND TRADEMARK OFFICE
CERTIFICATE OF CORRECTION

PATENT NO. : 5,756,315

DATED : May 26, 1998

INVENTOR(S): HIDEO MORI ET AL.

It is certified that error appears in the above-identified patent and that said Letters Patent is hereby corrected as shown below:

<u>COLUMN 34</u>

Line 13, "DATP." should read --dATP.--;

Signed and Sealed this

Twenty-fourth Day of October, 2000

Attest:

Q. TODD DICKINSON

*Attesting Officer*   *Director of Patents and Trademarks*